United States Patent
Otsu et al.

(10) Patent No.: US 11,583,694 B2
(45) Date of Patent: Feb. 21, 2023

(54) TREATMENT METHOD

(71) Applicant: TERUMO KABUSHIKI KAISHA, Tokyo (JP)

(72) Inventors: Keiko Otsu, Kanagawa (JP); Yuji Onimura, Shizuoka (JP); Keiichiro Yamamoto, Shizuoka (JP); Takanobu Ishizuka, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 114 days.

(21) Appl. No.: 17/318,354

(22) Filed: May 12, 2021

(65) Prior Publication Data

US 2021/0268302 A1  Sep. 2, 2021

Related U.S. Application Data

(62) Division of application No. 16/804,420, filed on Feb. 28, 2020, now Pat. No. 11,033,753.

(30) Foreign Application Priority Data

Feb. 28, 2019 (JP) .............................. JP2019-036838

(51) Int. Cl.
*A61N 5/06* (2006.01)
*A61M 25/10* (2013.01)
(Continued)

(52) U.S. Cl.
CPC ........ *A61N 5/0601* (2013.01); *A61B 17/3478* (2013.01); *A61M 5/158* (2013.01);
(Continued)

(58) Field of Classification Search
CPC .................. A61N 5/062; A61N 5/0601; A61N 2005/0659; A61N 2005/063; A61N 2005/0602

See application file for complete search history.

(56) References Cited

U.S. PATENT DOCUMENTS

2003/0114434 A1   6/2003   Chen et al.
2003/0130575 A1*  7/2003   Desai ................... A61K 9/0034
                                                          600/417

(Continued)

FOREIGN PATENT DOCUMENTS

JP      2001510806 A    8/2001
WO         9904810 A2    2/1999

*Primary Examiner* — Nathan R Price
*Assistant Examiner* — Courtney B Fredrickson
(74) *Attorney, Agent, or Firm* — Buchanan Ingersoll & Rooney PC

(57) ABSTRACT

A treatment method is disclosed capable of reducing the burden on a patient and enhancing the effect of killing tumor cells. The method includes administering an antibody-photosensitive substance into a vein; inserting an endoscope from a mouth, a nose, or an anus and bringing the endoscope to a vicinity of a tumor after the administering of the antibody-photosensitive substance into the vein; placing an optical fiber into the tumor or in the vicinity of the tumor; irradiating at least one of the tumor, the vicinity of the tumor, or a regional lymph node with a first near-infrared ray by the optical fiber; and irradiating the antibody-photosensitive substance bound to a tumor cell membrane in the tumor cell with a second near-infrared ray after the irradiating with the first near-infrared ray, the second near-infrared ray having a shorter wavelength than that of the first near-infrared ray.

20 Claims, 9 Drawing Sheets

(51) Int. Cl.
*A61B 17/34* (2006.01)
*A61M 5/158* (2006.01)
*A61M 5/14* (2006.01)
*A61B 8/08* (2006.01)
*A61B 8/12* (2006.01)
*A61B 1/05* (2006.01)
*A61B 1/005* (2006.01)

(52) U.S. Cl.
CPC ............ *A61M 25/10* (2013.01); *A61N 5/062* (2013.01); *A61B 1/005* (2013.01); *A61B 1/05* (2013.01); *A61B 8/085* (2013.01); *A61B 8/12* (2013.01); *A61M 2005/1403* (2013.01); *A61M 2025/105* (2013.01); *A61M 2025/1052* (2013.01); *A61M 2205/3375* (2013.01); *A61M 2210/12* (2013.01); *A61M 2230/50* (2013.01); *A61N 2005/0602* (2013.01); *A61N 2005/063* (2013.01); *A61N 2005/0659* (2013.01)

(56) References Cited

U.S. PATENT DOCUMENTS

| | | |
|---|---|---|
| 2006/0212099 A1 | 9/2006 | Riddell |
| 2006/0253178 A1 | 11/2006 | Masotti |
| 2010/0010482 A1 | 1/2010 | Neuberger |
| 2017/0043179 A1* | 2/2017 | Mandel ................ A61N 5/0616 |

* cited by examiner

TREATMENT METHOD

CROSS-REFERENCES TO RELATED APPLICATIONS

This application is a divisional of U.S. application Ser. No. 16/804,420 filed on Feb. 28, 2020, which claims priority to Japanese Application No. 2019-036838 filed on Feb. 28, 2019, the entire contents of which are incorporated herein by reference.

FIELD OF THE DISCLOSURE

The present disclosure generally relates to a treatment method for killing tumor cells.

BACKGROUND DISCUSSION

Although progress has been made in the clarification of the developmental mechanism, diagnostic methods, and treatments method of cancers, much of the advanced cancers cannot currently be cured. The development of new early diagnostic methods and treatment methods has been required for improvement of the present situation. Cancer immunotherapy is one of the expected treatment methods. In the cancer immunotherapy, T cells (CTL) which attack the cancer cells play a key role, and effective activity of CTL is considered to influence therapeutic effects. It is important in the activation of CTL that the cancer immunity cycle progresses rather smoothly. First, after the cancer cells are damaged and cancer antigens are released, antigen presentation is efficiently performed by antigen-presenting cells (dendritic cells and macrophages), thereby activating CTLs. Therefore, when the antigens are released in the cancer area, it is important to gather and activate more antigen-presenting cells (for example, see JP-T-2001-510806).

Examples of a method for activating antigen-presenting cells include a method for administering an adjuvant. However, compounds used as adjuvants are often toxic.

SUMMARY

A treatment method is disclosed, which is capable of reducing the relative burden on a patient and enhancing the effect of killing a tumor cell.

According to an aspect of the present disclosure, a treatment method is disclosed for killing a tumor cell, the method including inserting a catheter into a main artery of an organ having the tumor cell, administering an antibody-photosensitive substance into a vein before the insertion of the catheter or administering the antibody-photosensitive substance into the artery from the catheter after the insertion of the catheter, inserting an optical fiber into the catheter, reducing an influence of blood in the artery on a near-infrared ray, irradiating at least one of a tumor having the tumor cell, a vicinity of the tumor, or a regional lymph node with a first near-infrared ray by the optical fiber, and irradiating an antibody-photosensitive substance bound to a tumor cell membrane in the tumor cell with a second near-infrared ray having a shorter wavelength than that of the first near-infrared ray.

With the treatment method having the above-described configuration, it is possible to effectively irradiate at least one of the tumor, the vicinity of the tumor, or a regional lymph node with the first near-infrared ray by the optical fiber inserted into an artery near the tumor through the catheter. For this reason, more antigen-presenting cells can be gathered at an irradiation target site, and when the tumor cells are damaged, and the antigen is released, antigen presentation can be rather efficiently performed by more antigen-presenting cells, leading to T cell activation. Further, by the optical fiber inserted into an artery near the tumor, the antibody-photosensitive substance bound to the tumor cell can be effectively irradiated with the second near-infrared ray. For this reason, since the photosensitive substance of the antibody-photosensitive substance can cause a chemical reaction and damage tumor cells, the antigen is released in a state where more antigen-presenting cells are gathered, and the antigen presentation is efficiently performed, leading to T cell activation. As a result, the present treatment method can improve or recover the attack capability of immunity against cancer. Further, since there is no need to administer an adjuvant in order to activate the antigen-presenting cells, it is possible to reduce the burden on a patient due to side effects of the adjuvant.

According to another aspect of the present disclosure, a treatment method is disclosed, which includes inserting a catheter into a main artery of an organ having the tumor cell, inserting an optical fiber into the catheter, reducing an influence of blood in the artery on a near-infrared ray, irradiating at least one of a tumor having the tumor cell, a vicinity of the tumor, or a regional lymph node with a first near-infrared ray by the optical fiber, and administering an anti-cancer agent into a vein or administering the anti-cancer agent into the artery from the catheter.

With the treatment method having the above-described configuration, it is possible to effectively irradiate at least one of the tumor, the vicinity of the tumor, or a regional lymph node with the first near-infrared ray by the optical fiber inserted into an artery near the tumor through the catheter. For this reason, more antigen-presenting cells can be gathered at an irradiation target site, and when tumor cells are damaged and release the antigen, antigen presentation is efficiently performed by antigen-presenting cells, leading to the T cell activation. Further, in the present treatment method, as a method for damaging the tumor cell, the anti-cancer agent is administered intravenously or locally to an artery, so the antigen is released from the tumor cell in a state where the antigen-presenting cell gather in the tumor, thereby efficiently presenting the antigen by more antigen-presenting cells, leading to T cell activation. As a result, the present treatment method can improve or recover the attack capability of immunity against cancer. Therefore, the present treatment method can enhance the effect of killing a tumor cell. Further, since there is no need to administer an adjuvant in order to activate the antigen-presenting cells, it is possible to reduce the burden on a patient such as side effects due to the adjuvant. When the anti-cancer agent is locally administered, the anti-cancer agent can be allowed to act on tumor cells in a short time and efficiently. Further, since the anti-cancer agent can be administered in a relatively small amount only at a necessary place, the burden on the patient can be reduced.

In the reducing of the influence of blood in the artery on the near-infrared ray, a saline solution may be injected into the artery through the catheter to flush the blood in the artery. Thereby, the near-infrared ray emitted from an optical fiber becomes relatively difficult to receive the influence of blood. For this reason, the first near-infrared ray can rather effectively reach at least one of the tumor, the vicinity of the tumor, or the regional lymph node. Further, the second near-infrared ray can rather effectively reach the antibody-photosensitive substance bound to the tumor cell membrane.

The saline solution may be injected into the artery passing between a lumen of the catheter and the optical fiber. Thereby, the saline solution can be injected into the artery using the catheter in which the optical fiber is inserted without using another device.

In the reducing of the influence of blood in the artery on the near-infrared ray, a balloon disposed in the catheter may be inflated to block a blood flow in the artery. Thereby, the near-infrared ray emitted from an optical fiber becomes rather difficult to receive the influence of blood. For this reason, the first near-infrared ray can effectively reach at least one of the tumor, the vicinity of the tumor, or the regional lymph node. Further, the second near-infrared ray can effectively reach the antibody-photosensitive substance bound to the tumor cell membrane.

According to still another aspect of the present disclosure, a treatment method is disclosed for killing a tumor cell, the method including inserting an endoscope from a mouth, a nose, or an anus and bringing the endoscope to a vicinity of a tumor reachable from the mouth, the nose, or the anus, protruding a tubular elongated tube in which a lumen is formed from the endoscope, bringing the elongated tube into contact with the tumor having the tumor cell or puncturing the tumor with the elongated tube while checking a camera image and/or an ultrasound image obtained by the endoscope, bringing an optical fiber inserted into the lumen of the elongated tube into the tumor or the vicinity of the tumor, administering an antibody-photosensitive substance into a vein before the bringing of the endoscope to the vicinity of the tumor or administering the antibody-photosensitive substance into the tumor or the vicinity of the tumor from the elongated tube after the bringing of the elongated tube into contact with the tumor or puncturing with the elongated tube, irradiating at least one of the tumor, the vicinity of the tumor, or a regional lymph node with a first near-infrared ray by the optical fiber, and irradiating an antibody-photosensitive substance bound to a tumor cell membrane in the tumor cell with a second near-infrared ray having a shorter wavelength than that of the first near-infrared ray.

With the treatment method having the above-described configuration, it is possible to effectively irradiate at least one of the tumor, the vicinity of the tumor, or the regional lymph node with the first near-infrared ray from the optical fiber disposed inside the tumor or the vicinity of the tumor through the endoscope. For this reason, antigen-presenting cells can be gathered at the irradiation target site. Further, as a method of damaging tumor cells, the optical fiber inserted into the tumor or in the vicinity of the tumor can rather effectively irradiate the antibody-photosensitive substance bound to the tumor cells with the second near-infrared ray. Therefore, the photosensitive substance of the antibody-photosensitive substance can cause a chemical reaction and kill the tumor cells. Thereby, when antigen-presenting cells are gathered in the tumor, the antigen is released from the tumor cells, and antigen presentation is performed by more antigen-presenting cells, leading to subsequent T cell activation. As a result, the present treatment method can help improve or recover the attack capability of immunity against cancer. Further, since it is not necessary to administer an adjuvant to activate the antigen-presenting cells, the burden on the patient can be reduced.

According to still another aspect of the present disclosure, a treatment method is disclosed for killing a tumor cell, the method including puncturing a tumor having the tumor cell or a vicinity of the tumor percutaneously with a hollow needle while acquiring and checking an ultrasound image percutaneously, bringing an optical fiber inserted into a lumen of the needle into the tumor or the vicinity of the tumor, administering an antibody-photosensitive substance into a vein before the bringing of the needle to the vicinity of the tumor or administering the antibody-photosensitive substance into the tumor or the vicinity of the tumor from the needle after the bringing of the needle to the vicinity of the tumor, irradiating at least one of the tumor, the vicinity of the tumor, or a regional lymph node with a first near-infrared ray by the optical fiber, and irradiating an antibody-photosensitive substance bound to a tumor cell membrane in the tumor cell with a second near-infrared ray having a shorter wavelength than that of the first near-infrared ray.

With the treatment method having the above-described configuration, it is possible to rather effectively irradiate at least one of the tumor, the vicinity of the tumor, or the regional lymph node with the first near-infrared ray by the optical fiber disposed inside the tumor or the vicinity of the tumor via the needle. For this reason, antigen-presenting cells can be gathered at the irradiation target site. Further, as a method of damaging tumor cells, the optical fiber inserted into the tumor or in the vicinity of the tumor can rather effectively irradiate the antibody-photosensitive substance bound to the tumor cells with the second near-infrared ray. As a result, the photosensitive substance of the antibody-photosensitive substance can cause a chemical reaction and kill the tumor cells. As a result, when antigen-presenting cells are gathered in the tumor, the antigen is released from the tumor cells, and antigen presentation is performed by more antigen-presenting cells, leading to subsequent T cell activation. As a result, the present treatment method can help improve or recover the attack capability of immunity against cancer. Further, since it is not necessary to administer an adjuvant to activate the antigen-presenting cells, the relative burden on the patient can be reduced.

In the irradiating with the first near-infrared ray and/or the irradiating with the second near-infrared ray, the needle may have a light-transmitting portion capable of transmitting a near-infrared ray at a distal end, and the near-infrared ray may be emitted from the optical fiber located inside the needle through the light-transmitting portion. Thereby, the near-infrared rays emitted from the optical fiber can reach a wide range of the irradiation target site without being obstructed by the elongated tube.

In the irradiating with the first near-infrared ray and/or the irradiating with the second near-infrared ray, the needle may have a slit through which a near-infrared ray can be emitted at a distal end, and the near-infrared ray may be emitted from the optical fiber located inside the needle through the slit. Thereby, the near-infrared rays emitted from the optical fiber are not rather easily obstructed by the elongated tube and can reach a wide range of the irradiation target site.

According to still another aspect of the present disclosure, a treatment method is disclosed, which includes inserting an endoscope from a mouth, a nose, or an anus and bringing the endoscope to a vicinity of a tumor reachable from the mouth, the nose, or the anus, protruding a tubular elongated tube in which a lumen is formed from the endoscope, bringing the elongated tube into contact with the tumor or puncturing the tumor with the elongated tube while checking a camera image and/or an ultrasound image obtained by the endoscope, bringing an optical fiber inserted into the lumen of the elongated tube into the tumor or the vicinity of the tumor, irradiating at least one of the tumor, the vicinity of the tumor, or a regional lymph node with a first near-infrared ray by the optical fiber, and administering an anti-cancer agent into a vein or administering the anti-cancer agent into the tumor or the vicinity of the tumor from the elongated tube.

With the treatment method having the above-described configuration, it is possible to relatively effectively irradiate at least one of the tumor, the vicinity of the tumor, or the regional lymph node with the first near-infrared ray by the optical fiber disposed inside the tumor or the vicinity of the tumor through the endoscope. For this reason, antigen-presenting cells can be gathered at the irradiation target site. Further, in the present treatment method, anti-cancer agents can damage tumor cells and release the antigen, so that more antigen-presenting cells will present the antigen when the antigen is released. As a result, the present treatment method can help improve or recover the attack capability of immunity against cancer. Therefore, the present treatment method can enhance the effect of killing a tumor cell. Further, since there is no need to administer an adjuvant in order to activate the antigen-presenting cells, side effects of the adjuvant can be avoided and the relative burden on the patient can be reduced. When the anti-cancer agent is locally administered, the anti-cancer agent can be allowed to act on tumor cells in a rather short time and efficiently. Further, since the anti-cancer agent can be administered in a small amount only at a necessary place, the burden on the patient can be reduced.

According to still another aspect of the present disclosure, a treatment method is disclosed for killing a tumor cell, the method including puncturing a tumor having the tumor cell or a vicinity of the tumor percutaneously with a hollow needle while acquiring and checking an ultrasound image percutaneously, bringing an optical fiber inserted into a lumen of the needle into the tumor or the vicinity of the tumor, irradiating at least one of the tumor, the vicinity of the tumor, or a regional lymph node with a first near-infrared ray by the optical fiber, and administering an anti-cancer agent into a vein or administering the anti-cancer agent into the tumor or the vicinity of the tumor from the needle.

With the treatment method having the above-described configuration, it is possible to rather effectively irradiate at least one of the tumor, the vicinity of the tumor, or the regional lymph node with the first near-infrared ray by the optical fiber disposed inside the tumor or the vicinity of the tumor via the needle. For this reason, more antigen-presenting cells can be gathered at the irradiation target site. Further, in the present treatment method, in order to administer anti-cancer agents intravenously or locally, anti-cancer agents can damage tumor cells and release the antigen, so that more antigen-presenting cells will present the antigen when the antigen is released, leading to subsequent T cell activation. As a result, the present treatment method can help improve or recover the attack capability of immunity against cancer. Therefore, the present treatment method can enhance the effect of killing a tumor cell. Further, since there is no need to administer an adjuvant in order to activate the antigen-presenting cells, side effects of the adjuvant can be avoided and the relative burden on the patient can be reduced. When the anti-cancer agent is locally administered, the anti-cancer agent can be allowed to act on tumor cells in a short time and efficiently. Further, since the anti-cancer agent can be administered in a relatively small amount only at a necessary place, the relative burden on the patient can be reduced.

In the irradiating with the first near-infrared ray, the needle may have a light-transmitting portion capable of transmitting a near-infrared ray at a distal portion, and the first near-infrared ray may be emitted from the optical fiber located inside the needle through the light-transmitting portion. Thereby, the first near-infrared ray emitted from the optical fiber can reach a wide range of the irradiation target site without being obstructed by the needle.

In the irradiating with the first near-infrared ray, the needle may have a slit through which a near-infrared ray can be emitted at a distal portion, and the first near-infrared ray may be emitted from the optical fiber located inside the needle through the slit. Thereby, the first near-infrared ray emitted from the optical fiber can reach a relatively wide range of the irradiation target site without being obstructed by the needle.

In accordance with another aspect, a treatment method is disclosed for killing a tumor cell, the method comprising: administering an antibody-photosensitive substance into a vein; inserting an endoscope from a mouth, a nose, or an anus and bringing the endoscope to a vicinity of a tumor having the tumor cell reachable from the mouth, the nose, or the anus after the administering of the antibody-photosensitive substance into the vein; placing an optical fiber into the tumor or in the vicinity of the tumor; irradiating at least one of the tumor, the vicinity of the tumor, or a regional lymph node with a first near-infrared ray by the optical fiber; and irradiating the antibody-photosensitive substance bound to a tumor cell membrane in the tumor cell with a second near-infrared ray after the irradiating of the at least one of the tumor, the vicinity of the tumor, or the regional lymph node with the first near-infrared ray, the second near-infrared ray having a shorter wavelength than that of the first near-infrared ray.

In accordance with a further aspect, a treatment method is disclosed for killing a tumor cell, the method comprising: administering an antibody-photosensitive substance into a vein; inserting an elongated tube in a lumen of an endoscope from a mouth, a nose, or an anus and bringing the elongated tube and the endoscope to a vicinity of a tumor having the tumor cell reachable from the mouth, the nose, or the anus after the administering of the antibody-photosensitive substance into the vein; placing an optical fiber into the tumor or in the vicinity of the tumor via a lumen of the elongated tube; irradiating at least one of the tumor, the vicinity of the tumor, or a regional lymph node with a first near-infrared ray by the optical fiber; and irradiating the antibody-photosensitive substance bound to a tumor cell membrane in the tumor cell with a second near-infrared ray after the irradiating of the at least one of the tumor, the vicinity of the tumor, or the regional lymph node with the first near-infrared ray, the second near-infrared ray having a shorter wavelength than that of the first near-infrared ray.

BRIEF DESCRIPTION OF THE DRAWINGS

FIG. 3A shows a case when a near-infrared ray is emitted in a distal end direction, and FIG. 3B shows a case when a near-infrared ray is emitted in a direction orthogonal to an optical fiber.

FIG. 4A shows a case when a near-infrared ray is emitted in a distal end direction, and FIG. 4B shows a case when a near-infrared ray is emitted in a direction orthogonal to an optical fiber.

FIG. 6A shows a modification example of an elongated tube, and FIG. 6B shows another modification example of the elongated tube.

FIG. 9A shows a state when puncturing an outer needle into a tumor, and FIG. 9B shows a state when puncturing an inner needle into a tumor.

FIG. 12A shows a state when puncturing an outer needle into a tumor, and FIG. 12B shows a state when puncturing an inner needle into a tumor.

DETAILED DESCRIPTION

Figure 1:
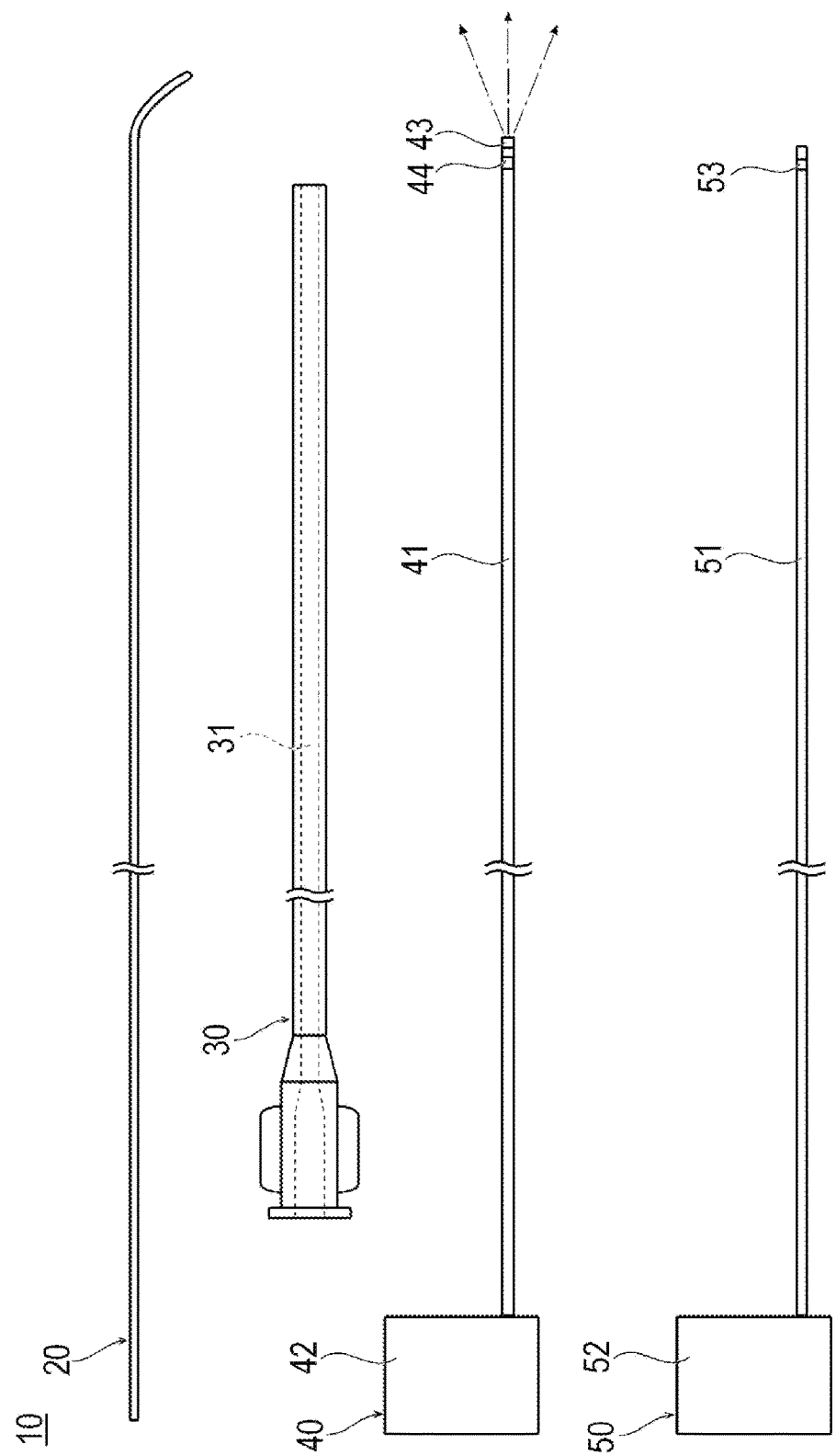
FIG. 1 is a plan view showing a treatment system used in a treatment method according to a first embodiment.

Embodiments of the present disclosure will be described below with reference to the drawings. Note that, the dimensions of the drawings are exaggerated for convenience of explanation and may differ from the actual dimensions. Further, in the present specification and drawings, components having substantially the same functional configuration are denoted by the same reference numerals, and redundant description is omitted. In the present specification, the side of a device that is inserted into a biological lumen is referred to as the "distal side" or "distal end", and the hand-side that is operated is referred to as the "proximal side" or "proximal end".

First Embodiment

The treatment method according to a first embodiment is a therapy that effectively combines a photolaser adjuvant and photoimmunotherapy, and is a therapy that can promote the cancer immunity cycle in a favorable turn and improve or recover the attack capability of immunity against cancer. In the treatment method according to the present embodiment, antigen-presenting cells can be gathered around the tumor by irradiation with a near-infrared ray, for example, having a wavelength of about 1064 nm. Photoimmunotherapy is a therapy that kills target cells by transvascularly irradiating the antibody-photosensitive substance bound to the cell membrane of the target cell with a near-infrared ray. The target cell can be a tumor cell such as a cancer cell. In this treatment method, an antibody-photosensitive substance obtained by binding an antibody that specifically binds only to a specific antigen on the surface of a tumor cell and a photosensitive substance that is paired with the antibody is used as a drug. The antibody is not particularly limited, and examples of the antibody can include panitumumab, trastuzumab, HuJ591, and the like. The photosensitive substance can be, for example hydrophilic phthalocyanine, which is a substance (IR700) that reacts with a near-infrared ray having a wavelength of around 700 nm, but the photosensitive substance is not limited to hydrophilic phthalocyanine. IR700 absorbs light when it receives near-infrared rays having, for example, a wavelength of about 660 nm to 740 nm, generates a chemical change, and generates heat to kill tumor cells. The treatment method according to the first embodiment can be suitable for cancer treatment of organs that are difficult to be irradiated with a near-infrared ray from the body surface because they are separated from the body surface, for example. The treatment method according to the first embodiment can be suitably used for the treatment of, for example, liver cancer and lung cancer.

In the treatment method according to the first embodiment, as shown in FIG. 1, a treatment system 10 that can be inserted into a blood vessel is used for transvascularly irradiating at least one of the tumor, the vicinity of the tumor, or a regional lymph node with a near-infrared ray. First, the treatment system 10 will be described.

The treatment system 10 can include a guide wire 20, a catheter 30, a light irradiation device 40 that can be inserted into the catheter 30, and a measurement device 50 that can be inserted into the catheter 30.

The guide wire 20 can be a relatively long wire for guiding the catheter 30 to a target position in the living body. The catheter 30 is a micro-catheter, for example, and has a lumen 31 penetrating from the distal end to the proximal end. A micro-catheter is a relatively thin catheter that can be inserted into a peripheral blood vessel of an organ to be treated. The diameter of the micro-catheter can be, for example, about 0.5 mm to 1.0 mm. Note that, the catheter 30 may be a catheter 30 thicker than a micro-catheter depending on the place to be treated. Further, as shown in FIG. 4, the catheter 30 may be a balloon catheter 30 including an inflatable balloon 32 at the distal portion. The balloon catheter 30 has a second lumen 33 for supplying a fluid for inflation to the balloon 32.

Figure 3A:
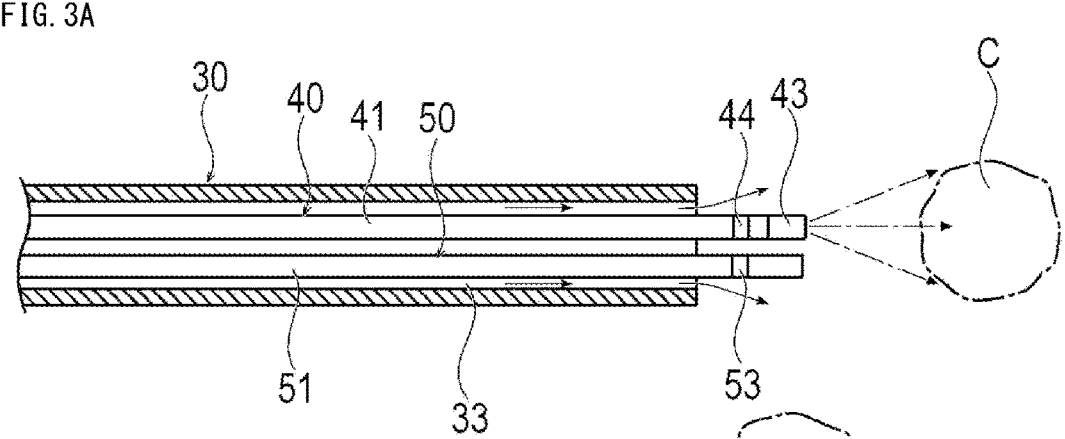
FIGS. 3A and 3B are cross-sectional views showing a treatment system when the liver cancer is treated, where

The light irradiation device 40 includes an optical fiber 41 and a light output unit 42 that supplies near-infrared rays to the optical fiber 41, as shown in FIGS. 1 and 3A. The light output unit 42 can output a near-infrared ray having any wavelength to the optical fiber 41 with any dose. In accordance with an exemplary embodiment, the light output unit 42 can selectively output a first near-infrared ray for the photolaser adjuvant and a second near-infrared ray for the photoimmunotherapy to the optical fiber 41. The wavelength of the first near-infrared ray for the photolaser adjuvant is longer than the second near-infrared ray for photoimmunotherapy. The light output unit 42 may be capable of outputting both the first near-infrared ray and the second near-infrared ray simultaneously. The light output unit 42 can perform output to the optical fiber 41 so that the first near-infrared ray having, for example, a wavelength of about 1064 nm can be emitted. Further, the light output unit 42 outputs to the optical fiber 41 so that the second near-infrared ray can be emitted at a wavelength of 660 nm to 740 nm, for example, with a dose of 1 $Jcm^{-2}$ to 50 $Jcm^{-2}$. The optical fiber 41 that outputs near-infrared rays may be composed of a single fiber or may be composed of a plurality of bundled fibers. The optical fiber 41 is preferably attachable and detachable to and from the light output unit 42 but is not limited to being attachable and detachable to and from the light output unit 42. An irradiation unit 43 for irradiating with light is provided at the distal end of the optical fiber 41. An orientation marker 44 is provided at the distal portion of the optical fiber 41.

Figure 3B:
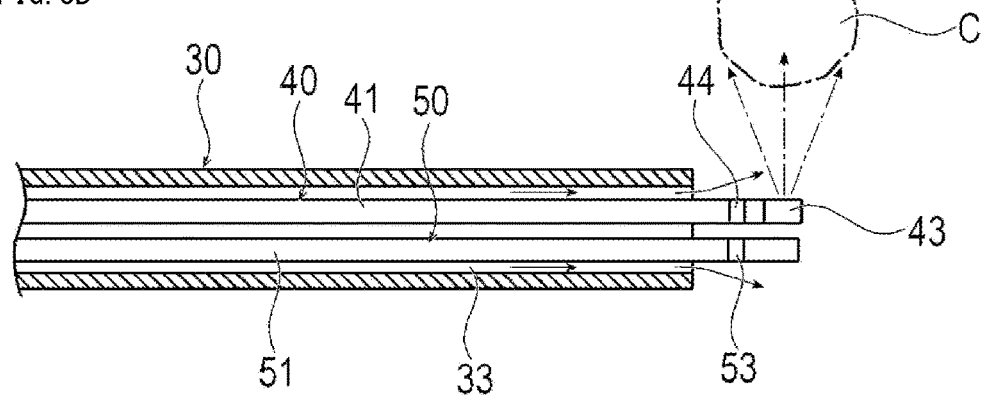

The irradiation unit 43 emits light that entered from the proximal side of the optical fiber 41 to the outside. The irradiation unit 43 can be configured by, for example, a lens, a diffuser, a mirror, and the like. The irradiation unit 43 is appropriately designed so as to emit a near-infrared ray at a predetermined irradiation angle in a predetermined direction using a lens, a diffuser, a mirror, or the like. Note that, the structure of the irradiation unit 43 is not limited as long as it can emit light to the outside. For example, as shown in FIG. 3A, the irradiation unit 43 emits a near-infrared ray at a predetermined irradiation angle in the distal end direction. Note that, the irradiation direction (the direction in which the center of the irradiation angle is located) is not particularly limited. For example, the irradiation unit 43 may emit the near-infrared ray in a direction substantially orthogonal to the optical fiber 41 as shown in FIG. 3B.

The orientation marker 44 is a site for an operator to check a position in the body. The orientation marker 44 is formed of, for example, a radiopaque material. The radiopaque material is, for example, a metal material such as a metal such as gold, platinum, tungsten, or an alloy containing these metallic materials. Thereby, the operator can check the position of the orientation marker 44 under X-ray contrast outside the body. Note that, the orientation marker 44 may not be an X-ray contrast marker as long as the operator can check the position in the body.

As shown in FIGS. 1 and 3A, the measurement device 50 is a device that monitors in real time that a tumor C having target cells can be irradiated with a near-infrared ray. The measurement device 50 is, for example, a temperature measurement device that can measure the temperature of the tumor C in a non-contact manner or in a contact manner. The measurement device 50 includes, for example, an optical fiber for measurement 51, an optical measurement unit 52 that receives light detected by the optical fiber for measurement 51, and a measurement marker 53 that is positioned at the distal portion of the optical fiber for measurement 51. The optical fiber for measurement 51 receives an infrared ray emitted from an object whose temperature has risen at the distal portion and transmits the infrared ray to the optical measurement unit 52. The optical measurement unit 52 can detect the temperature of the object in a non-contact manner from the measured second infrared ray dose or the like.

Note that, the optical fiber for measurement 51 may be shared with the optical fiber 41 of the light irradiation device 40. That is, the temperature of the tumor C may be measured using the optical fiber 41 of the light irradiation device 40.

The measurement device 50 is not limited to the temperature measurement device using the optical fiber 41 as long as it is possible to monitor that the tumor cell to which the antibody-photosensitive substance is bound is irradiated with the second near-infrared ray. For example, a contact-type temperature measurement device using a thermocouple or a hardness measurement device 50 using ultrasound waves may be used. When the measurement device 50 is a hardness measurement device 50 using ultrasound waves, an ultrasound probe is provided at the distal portion of an elongated tubular body that can be inserted into the catheter 30. The hardness measurement device 50 transmits an ultrasound wave to the outside by a probe and receives a reflected wave of the ultrasound wave to calculate a tomographic image of the tissue. The hardness measurement device 50 can detect a change in the hardness of the tumor C including dead tumor cells from the change in the luminance of the tomographic image. Alternatively, the measurement device 50 may be a sensor that can detect an elastic change of a tumor C including dead tumor cells and a change in blood flow.

Next, the treatment method according to the first embodiment will be described taking the case of treating liver cancer as an example. Note that, this description is not intended to limit the organs to be treated.

Figure 2:
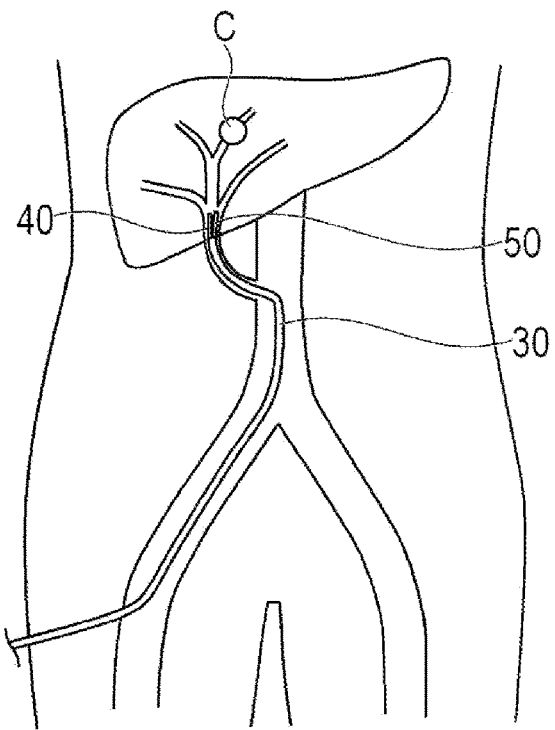
FIG. 2 is a schematic view showing a state inside a body when treating liver cancer by the treatment method according to the first embodiment.

First, an antibody-photosensitive substance is administered intravenously. For example, after about 12 hours to 36 hours from intravenous administration, the operator inserts the guide wire 20 into the blood vessel from the femoral artery, brachial artery, radial artery, and the like, as shown in FIG. 2. Next, the proximal end of the guide wire 20 is inserted into the lumen 31 of the catheter 30, and the catheter 30 is inserted into the blood vessel along the guide wire 20. Next, the catheter 30 is inserted into the hepatic artery, which is the main artery (for example, nutrient artery) of the liver in which the tumor C is formed, with the guide wire 20 in advance. Thereafter, the operator removes the guide wire 20 from the catheter 30. Note that, in the treatment of lung cancer, the main artery of the lung is the bronchial artery.

Next, the operator inserts the optical fiber 41 into the lumen 31 from the proximal side of the catheter 30. As shown in FIG. 3A, the distal portion of the optical fiber 41 protrudes from the catheter 30 toward the distal side. Next, the operator causes the position of the orientation marker 44 of the optical fiber 41 to reach the target position while checking the position of the orientation marker 44 of the optical fiber 41 under X-ray contrast. The target position is a position close to the tumor C and capable of irradiating at least one of the tumor C, the vicinity of the tumor, or the regional lymph node with the first near-infrared ray. A regional lymph node is a group of lymph nodes that have a lymphatic tract directly connected to the primary lesion.

Next, the operator inserts the optical fiber for measurement 51 into the lumen 31 from the proximal side of the catheter 30. The distal portion of the optical fiber for measurement 51 protrudes from the catheter 30 toward the distal side. Next, the operator causes the position of the measurement marker 53 of the optical fiber for measurement 51 to reach the target position while checking the position of the measurement marker 53 of the optical fiber for measurement 51 under X-ray contrast. The target position is a position close to the tumor C where the cancer cell is present and the temperature of the tumor C can be measured. The optical fiber for measurement 51 is preferably disposed at a position where the emission of the near-infrared ray from the optical fiber 41 is not obstructed.

Next, the operator supplies the saline solution to the lumen 31 from the proximal side of the catheter 30. At this time, for example, the operator connects the Y connector to the hub located at the proximal portion of the catheter 30, and supplies the saline solution from a port different from the port from which the guide wire 20 is led out. The saline solution flows into the hepatic artery through a gap in the lumen 31 in which the optical fiber 41 and the optical fiber for measurement 51 are inserted. Thereby, the saline solution is injected (flushed) from the catheter 30 to the hepatic artery. For this reason, blood in the hepatic artery where the optical fiber 41 and the optical fiber for measurement 51 are located is pushed away, and the hepatic artery is temporarily filled with the saline solution. The saline solution is injected into the artery through the lumen 31 of the catheter 30 and the optical fiber 41. Thereby, the saline solution can be injected into the hepatic artery using the catheter 30 in which the optical fiber 41 is inserted without using another device.

Figure 4A:
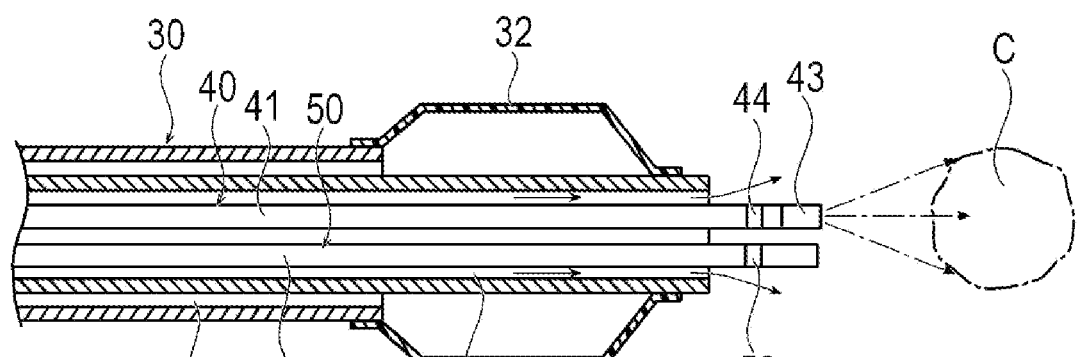
FIGS. 4A and 4B are cross-sectional views showing the treatment system when the liver cancer is treated using a balloon catheter, where

As shown in FIG. 4A, when the catheter 30 has the balloon 32, the balloon 32 may be inflated before, during, or after flushing the saline solution. Thereby, the blood flow in the hepatic artery is blocked and the hepatic artery is temporarily filled with the saline solution. For this reason, the hepatic artery can be more reliably filled with the saline solution. Note that, the operator may inflate the balloon 32 without flushing the saline solution.

In accordance with an exemplary embodiment, after filling the hepatic artery with the saline solution or blocking the blood flow in the hepatic artery, the operator may observe the hepatic artery with the optical fiber 41 or the optical fiber for measurement 51. Thereby, the operator can accurately check that the hepatic artery is filled with the saline solution and/or that the blood flow in the hepatic artery is blocked. Note that, observation of blood in the hepatic artery using the optical fiber 41 or the optical fiber for measurement 51 may not be performed.

Next, as shown in FIG. 3A or 4A, at least one of the tumor C, the vicinity of the tumor, or the regional lymph node is irradiated with the first near-infrared ray from the optical fiber 41. At this time, since the hepatic artery is filled with the saline solution and/or the blood flow in the hepatic artery is blocked, the irradiation with the first near-infrared ray is hardly affected by blood. For this reason, the first near-infrared ray can effectively reach at least one of the tumor C, the vicinity of the tumor, or the regional lymph node. When irradiating with the first near-infrared ray from the optical fiber 41, the first near-infrared ray is directly emitted from the optical fiber 41 to the biological tissue. That is, for example, the first near-infrared ray is not indirectly emitted from the inside of the balloon through the balloon. For this reason, the target place can be effectively irradiated with the first near-infrared ray.

Figure 4B:
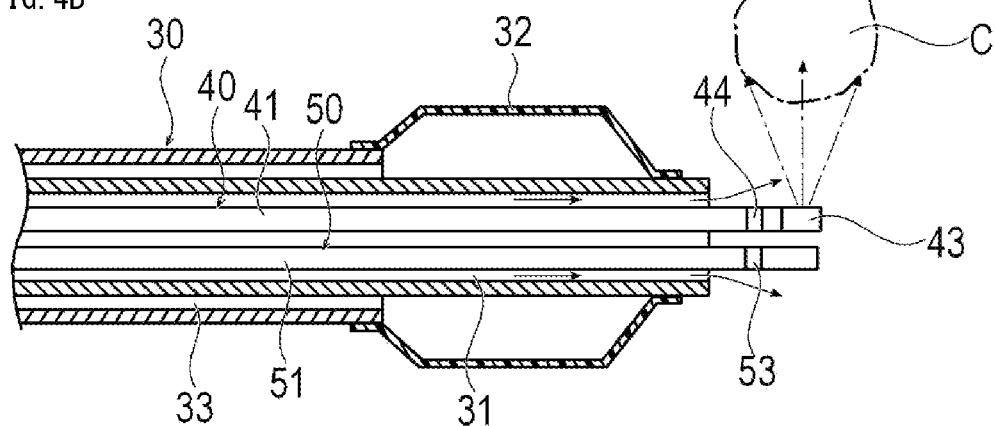

The irradiation direction of the first near-infrared ray from the optical fiber 41 is the distal end direction of the optical fiber 41. Alternatively, as shown in FIG. 3B or 4B, the irradiation direction of the first near-infrared ray may be a direction orthogonal to the axial direction of the optical fiber 41. The operator can appropriately select the optical fiber 41 to be used according to at least one position of the tumor C that is an irradiation target site for the blood vessel into which the optical fiber 41 is inserted, the vicinity of the tumor, or the regional lymph node.

When the irradiation target site that is at least one of the tumor C, the vicinity of the tumor, or the regional lymph node is irradiated with the first near-infrared ray, more antigen-presenting cells can be gathered in the irradiation target site. For this reason, when the tumor cells are damaged and the antigens are released, more antigen-presenting cells will present the antigen, leading to subsequent T cell activation. As a result, the attack capability of immunity against cancer can be improved or recovered. The operator stops the irradiation with the first near-infrared ray by the optical measurement unit 52 after a predetermined time has elapsed since the start of the irradiation with the first near-infrared ray. The optical measurement unit 52 may have an irradiation time of the second near-infrared ray set in advance. The irradiation time of the first near-infrared ray is not particularly limited, but can be, for example, 2 minutes to 15 minutes.

Next, the temperature of the tumor C is measured by the optical fiber for measurement 51 while irradiating the tumor C or the vicinity of the tumor C with the second near-infrared ray from the optical fiber 41. The operator may change the direction and position of the optical fiber 41 before emitting the second near-infrared ray. This is because the site where the irradiation with the first near-infrared ray is effective and the site where the irradiation with the second near-infrared ray is effective may be different. In accordance with an exemplary embodiment, the irradiation with the second near-infrared ray can start 12 hours to 36 hours after intravenous administration. The start of the irradiation with the second near-infrared ray is not particularly limited, but can be started, for example, after 1 minutes to 60 minutes have elapsed from the end of the irradiation with the first near-infrared ray. The operator may inject the saline solution again from the catheter 30 into the hepatic artery before emitting the second near-infrared ray from the optical fiber 41.

The operator can monitor that the tumor cell to which the antibody-photosensitive substance is bound is irradiated with the second near-infrared ray by continuing the temperature measurement of the tumor C. At this time, since the hepatic artery is filled with the saline solution and/or the blood flow in the hepatic artery is blocked, the irradiation with the second near-infrared ray and temperature measurement are hardly affected by blood. For this reason, the second near-infrared ray can effectively reach the antibody-photosensitive substance bound to the tumor cell membrane. Therefore, the irradiation with the second near-infrared ray and temperature measurement can be performed rather effectively. When irradiating with the second near-infrared ray from the optical fiber 41, the second near-infrared ray is directly emitted from the optical fiber 41 to the biological tissue. That is, the second near-infrared ray is not indirectly emitted from the inside of the balloon through the balloon, for example. For this reason, the tumor cell to which the antibody-photosensitive substance is bound can be effectively irradiated with the second near-infrared ray.

The irradiation direction of the second near-infrared ray from the optical fiber 41 is the distal end direction of the optical fiber 41. Alternatively, as shown in FIG. 3B or 4B, the second near-infrared ray may be in a direction orthogonal to the axial direction of the optical fiber 41. The operator can appropriately select the optical fiber 41 to be used according to the position of the tumor C or the vicinity of the tumor C with respect to the blood vessel into which the optical fiber 41 is inserted. Note that, the optical fiber 41 that emits the first near-infrared ray and the optical fiber 41 that emits the second near-infrared ray are not the same and may be different.

The operator continues the irradiation with the second near-infrared ray while checking the death of the tumor cells by the irradiation with the second near-infrared ray based on the temperature of the tumor C monitored by the measurement device 50. The operator may adjust the irradiation direction and position by operating the optical fiber 41 at hand during emission of the second near-infrared ray.

When it is determined that the tumor cells have been sufficiently killed, when it is determined that further irradiation is not desirable, or when a predetermined time has elapsed, the operator stops the irradiation with the second near-infrared ray and stops monitoring by the measurement device 50. In order to make the determination that the tumor cells have been sufficiently killed easier, a temperature threshold value that is a condition for stopping the irradiation may be set in advance. When the temperature of the tumor C to be measured exceeds the threshold value, the operator can rather easily determine the stop of the irradiation with the second near-infrared ray. The threshold value may be set in the optical measurement unit 52. Thereby, the optical measurement unit 52 can give a notice to the operator via the monitor, the speaker, or the like when the temperature of the tumor C to be measured exceeds the threshold value. Note that, the condition for stopping the irradiation with the second near-infrared ray may not be the temperature of the tumor C exceeding the threshold value, but the width (volume or area) of the tumor C exceeding the threshold value. Alternatively, the optical measurement unit 52 may have an irradiation time of the second near-infrared ray set in advance.

Next, the operator specifies the position of the tumor C that has been irradiated with the second near-infrared ray, and records the position of the tumor C in the record as electronic data. The position of the tumor C is preferably recorded as electronic data so as to correspond to the position information of data such as CT image and MRI image of the patient acquired in advance. Thereby, the subsequent procedure can be advanced smoothly, and post-operative follow-up can be effectively performed. For example, when irradiating a plurality of tumors C with the near-infrared ray, the tumor C that has been irradiated with the near-infrared ray can be accurately identified, so that the irradiation of all tumors C can be performed relatively smoothly and reliably. Next, the operator removes the catheter 30 together with the optical fiber 41 and the measurement device 50 from the skin.

The monitoring of the irradiation with the second near-infrared ray may be performed using, instead of the optical fiber 51 for measurement, the optical fiber 41 for near-infrared ray irradiation, a temperature measurement device having a thermocouple, or a hardness measurement device using ultrasound waves. Further, the monitoring of the irradiation with the second near-infrared ray may be performed by a sensor located outside the body or a sensor inserted in a lumen in a living body.

As described above, the treatment method according to the first embodiment is a treatment method for killing a tumor cell, the method including inserting the catheter 30 into the main artery of an organ having the tumor cell, administering the antibody-photosensitive substance into a vein before the insertion of the catheter 30, inserting the optical fiber 41 into the catheter 30, reducing an influence of blood in the artery on the near-infrared ray, irradiating at least one of the tumor C having the tumor cell, the vicinity of the tumor C, or the regional lymph node with the first near-infrared ray by the optical fiber 41, and irradiating the antibody-photosensitive substance bound to a tumor cell membrane in the tumor cell with the second near-infrared ray having a shorter wavelength than that of the first near-infrared ray.

With the treatment method having the above-described configuration, it is possible to effectively irradiate at least one of the tumor C, the vicinity of the tumor C, or a regional lymph node with the first near-infrared ray by the optical fiber 41 inserted into an artery near the tumor C through the catheter 30. For this reason, since more antigen-presenting cells can be gathered at the irradiation target site, more antigen-presenting cells present the antigen when the tumor cells are damaged and the antigen is released, leading to T cell activation. As a result, the present treatment method can improve or recover attack capability of immunity against cancer. Further, the second optical fiber 41 inserted into the artery close to the tumor C can irradiate the antibody-photosensitive substance bound to the tumor cell with the second near-infrared ray. For this reason, the photosensitive substance of the antibody-photosensitive substance generates a chemical reaction and can enhance the effect of killing tumor cells. Further, since there is no need to administer an adjuvant in order to activate the antigen-presenting cells, it is possible to reduce the relative burden on a patient such as side effects due to the adjuvant.

Second Embodiment

Similar to the treatment method according to the first embodiment, the treatment method according to a second embodiment is applied to cancer treatment of an organ that can be reached transvascularly. The treatment method according to the second embodiment can be suitably used, for example, for the treatment of liver cancer, lung cancer, and the like. Note that, the treatment method according to the second embodiment is different from the first embodiment in that the antibody-photosensitive substance is not administered intravenously but locally to the nutrient blood vessel of the organ where the tumor C is formed. Note that, the treatment system is the same as the treatment system 10 used in the treatment method according to the first embodiment.

In the treatment method according to the second embodiment, the operator inserts the catheter 30 into the hepatic artery while leading the guide wire 20 from, for example, the femoral artery, brachial artery, radial artery, and the like without intravenous administration of the antibody-photosensitive substance. Next, the operator removes the guide wire 20 from the catheter 30. Next, the operator locally administers the antibody-photosensitive substance from the proximal side of the catheter 30 into the hepatic artery via the lumen 31. Note that, in the case of treatment of lung cancer, an antibody-photosensitive substance is locally administered to the bronchial artery, which is the nutrient artery of the lung to be treated.

After local administration of the antibody-photosensitive substance to the hepatic artery, the operator waits until the antibody-photosensitive substance binds to the target cell membrane. When an antibody-photosensitive substance is locally administered to the nutrient artery of the organ where the tumor C to be treated is present, the time until the antibody-photosensitive substance binds to the target cell membrane is much shorter than that for intravenous administration, and is considered to be, for example, about 5 minutes to 10 minutes.

Next, the operator inserts the optical fiber 41 into the lumen 31 from the proximal side of the catheter 30. Thereafter, similarly to the treatment method according to the first embodiment, the first infrared ray and the second infrared ray are emitted using the optical fiber 41. Note that, since the subsequent procedure is the same as the treatment method according to the first embodiment, the description of subsequent procedure is omitted. The irradiation with the second near-infrared ray is started, for example, about 5 minutes to 10 minutes after the local administration of the antibody-photosensitive substance. The irradiation with the second near-infrared ray may not be started after about 5 minutes to 10 minutes.

As described above, the treatment method according to the second embodiment is a treatment method for killing a tumor cell, the method including inserting the catheter 30 into the main artery of an organ having the tumor cell, administering the antibody-photosensitive substance into an artery from the catheter 30 after the insertion of the catheter 30, inserting the optical fiber 41 into the catheter 30, reducing an influence of blood in the artery on the near-infrared ray, irradiating at least one of the tumor C having the tumor cell, the vicinity of the tumor C, or the regional lymph node with the first near-infrared ray by the optical fiber 41, and irradiating the antibody-photosensitive substance bound to a tumor cell membrane in the tumor cell with the second near-infrared ray having a shorter wavelength than that of the first near-infrared ray.

With the treatment method having the above-described configuration, it is possible to effectively irradiate at least one of the tumor C, the vicinity of the tumor C, or a regional lymph node with the first near-infrared ray from the optical fiber 41 inserted into an artery near the tumor C through the catheter 30. For this reason, more antigen-presenting cells can be gathered at the irradiation target site. Further, as a method of damaging tumor cells, the optical fiber 41 inserted into the artery close to the tumor C can irradiate the antibody-photosensitive substance bound to the tumor cell with the second near-infrared ray. Thereby, the photosensitive substance of the antibody-photosensitive substance can cause a chemical reaction and damage the tumor cells. Therefore, when antigens are released from damaged tumor cells, the antigens are efficiently presented by a larger number of antigen-presenting cells, leading to T cell activation. As a result, the present treatment method can improve or recover attack capability of immunity against cancer. Further, since it is not necessary to administer an adjuvant to activate the antigen-presenting cells, it is possible to reduce the relative burden on the patient such as side effects of the adjuvant. Furthermore, since the antibody-photosensitive substance is locally administered, the antibody-photosensitive substance can act on tumor cells in a relatively short time and rather efficiently. In addition, since the antibody-photosensitive substance can be administered in a small amount only at a necessary place, the relative burden on the patient can be reduced.

Third Embodiment

The treatment method according to a third embodiment is applied to cancer treatment of organs that can be reached from the mouth, nose, or anus using an endoscope. The treatment method according to the third embodiment can be suitably used for the treatment of, for example, pancreatic cancer, lung cancer, stomach cancer, duodenal cancer, esophageal cancer, colon cancer, and the like.

Figure 5:
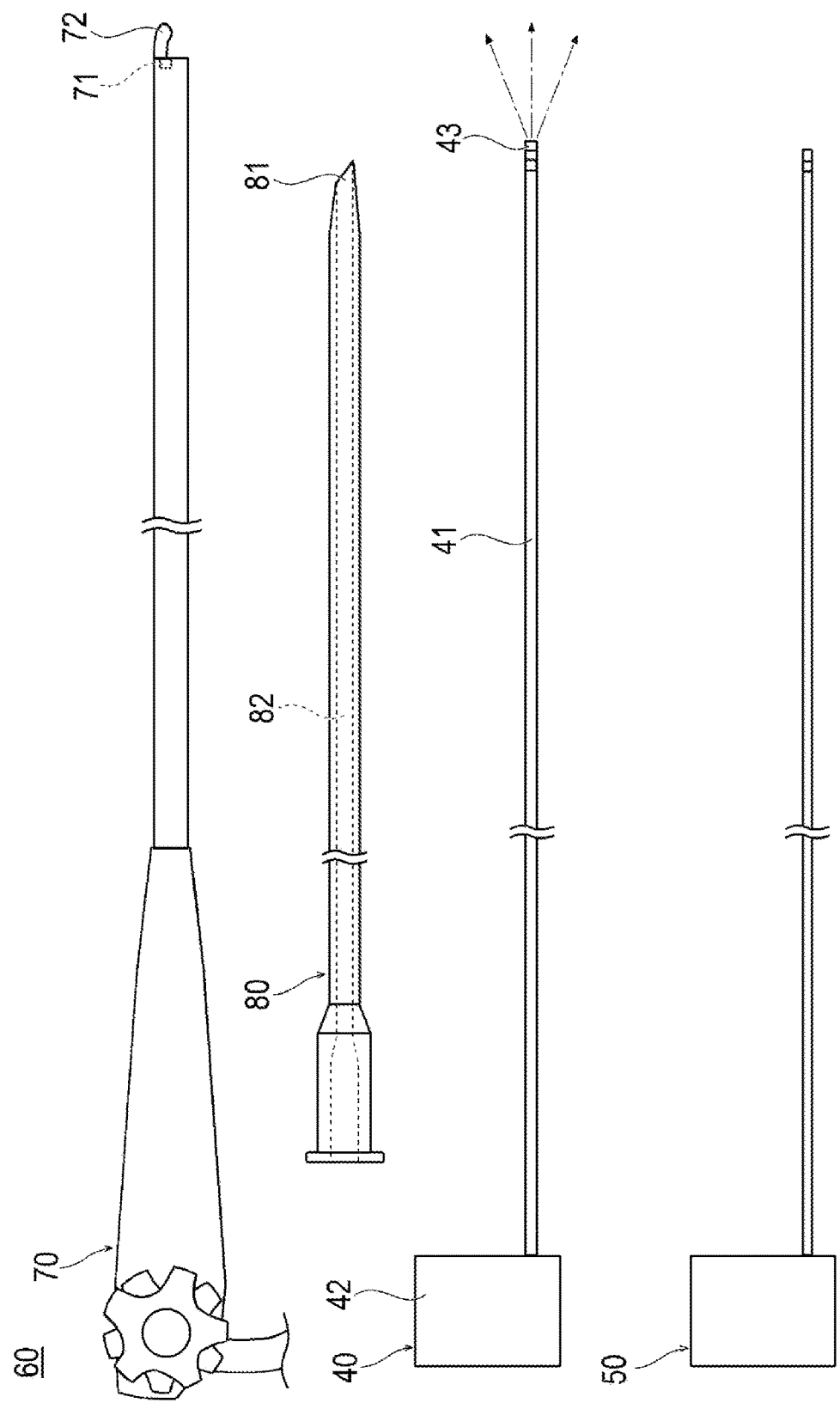
FIG. 5 is a plan view showing a treatment system used in a treatment method according to a third embodiment.

In the treatment method according to the third embodiment, as shown in FIG. 5, a treatment system 60 that can be inserted from the mouth, nose, or anus is used to emit the first near-infrared ray and the second near-infrared ray. First, the treatment system 60 will be described.

The treatment system 60 includes an endoscope 70, an elongated tube 80 that can be inserted into the endoscope 70, the light irradiation device 40 that can be inserted into the elongated tube 80, and the measurement device 50 that can be inserted into the elongated tube 80.

The endoscope 70 can be inserted from the mouth, nose, or anus, and a camera 71 capable of acquiring an image and an ultrasound imaging device 72 are disposed at the distal portion.

The endoscope 70 can acquire an image with the camera 71 in real time. Further, the endoscope 70 can acquire an ultrasound image in real time by the ultrasound imaging device 72. The endoscope 70 can acquire at least one of a camera image and an ultrasound image.

The elongated tube 80 has a sharp needle tip 81 formed at the distal end. The elongated tube 80 is hollow, and a lumen 82 penetrating from the needle at the distal end to the proximal end is formed.

As in the first embodiment, the measurement device 50 is a temperature measurement device using the optical fiber 41 that irradiates near-infrared rays, a temperature measurement device using the optical fiber for measurement 51 different from the optical fiber 41, a temperature measurement device using a thermocouple, or a hardness measurement device using ultrasound waves. Unlike the first embodiment, the measurement device 50 in the second embodiment can measure the temperature in contact with the tumor C. Therefore, a temperature measurement device using a thermocouple can be suitably used as the measurement device 50. Alternatively, the measurement device 50 may be a sensor that can detect an elastic change of a tumor C having dead tumor cells or a change in blood flow.

Next, the treatment method according to the third embodiment will be described taking the case of treating stomach cancer as an example. Note that, this description is not intended to limit the organs to be treated.

Figure 7:
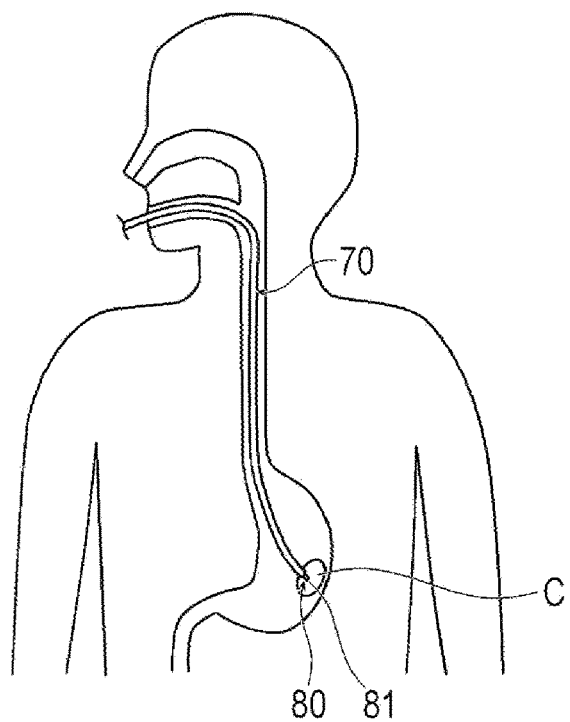
FIG. 7 is a schematic view showing a state inside a body when treating stomach cancer by the treatment method according to the third embodiment.
Figure 8:
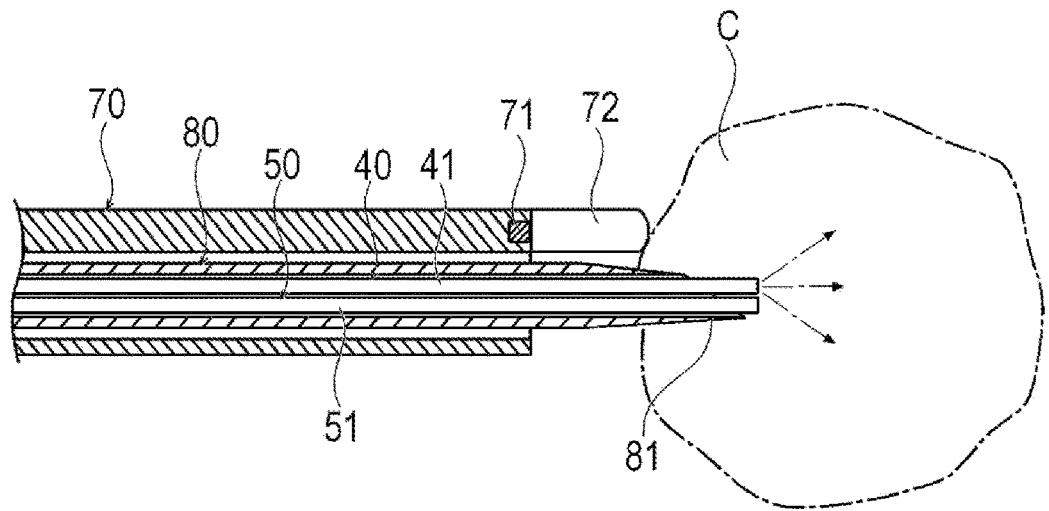
FIG. 8 is a cross-sectional view showing the treatment system when treating stomach cancer.

First, an antibody-photosensitive substance is administered intravenously. In accordance with an exemplary embodiment, for example, after about 12 hours to 36 hours have elapsed from intravenous administration, the operator inserts the endoscope 70 from the mouth or nose as shown in FIG. 7 so that the endoscope 70 reaches the vicinity of the stomach cancer. Next, the operator inserts the elongated tube 80 into the proximal portion of the endoscope 70 and causes the elongated tube 80 to protrude from the distal portion of the endoscope 70. Next, as shown in FIG. 8, the operator puncture the needle tip 81 of the elongated tube 80 in contact with the tumor C while checking the camera image and/or ultrasound image of the endoscope 70. Thereby, the position of the elongated tube 80 can be fixed with respect to the tumor C. Note that, the elongated tube 80 may be inserted into the mouth, nose, or anus together with the endoscope 70 in a state in which the elongated tube 80 is disposed in advance in the endoscope 70.

Next, the operator inserts the optical fiber 41 and the measurement device 50 from the proximal side of the lumen 82 of the elongated tube 80. The distal portion of the optical fiber 41 and the measurement device 50 protrudes from the needle tip 81 toward the distal side inside the hole formed in the tumor C by the needle tip 81. Note that, the optical fiber 41 and the measurement device 50 do not have to protrude from the needle tip 81. Further, the optical fiber 41 and/or the measurement device 50 may be inserted into the endoscope 70 in a state in which the optical fiber 41 and/or the measurement device 50 are disposed in advance in the elongated tube 80.

Next, the operator performs irradiation of at least one of the tumor C, the vicinity of the tumor C, or the regional lymph node with the first near-infrared ray from the optical fiber 41. Thereby, many antigen-presenting cells can be gathered in the irradiation target site. As a result, when tumor cells are damaged and release antigens, antigens can be efficiently presented by more antigen-presenting cells, leading to T cell activation. For this reason, the attack capability of immunity against cancer can be improved or recovered. The operator stops the irradiation with the first near-infrared ray after a predetermined time has elapsed since the start of the irradiation with the first near-infrared ray.

Next, the operator measures the temperature or hardness of the tumor C with the measurement device 50 while irradiating with the second near-infrared ray from the optical fiber 41. By continuing the measurement of tumor C, it is possible to monitor in real time that the tumor cell to which the antibody-photosensitive substance is bound is irradiated with the second near-infrared ray. The irradiation with the second near-infrared ray starts, for example, 12 hours to 36 hours after intravenous administration.

The irradiation direction of near-infrared rays from the optical fiber 41 is appropriately selected. For example, the irradiation direction of the near-infrared rays may be the distal end direction of the optical fiber 41, the direction orthogonal to the axial direction of the optical fiber 41, or all directions (i.e., the distal end direction, the direction orthogonal to the axial direction, and the directions between the distal end direction and the direction orthogonal to the axial direction). The operator can appropriately select the optical fiber to be used according to the near-infrared ray irradiation target site.

The operator continues the irradiation with the second near-infrared ray while checking the death of the tumor cells by the irradiation with the second near-infrared ray by monitoring with the measurement device 50. The operator can adjust the irradiation direction by operating the optical fiber 41 at hand during the irradiation with the second near-infrared ray.

Note that, the operator may cause the needle tip 81 of the elongated tube 80 to come in contact with the tumor C without puncturing the tumor C. Even if the elongated tube 80 is only in contact with the tumor C, the position of the elongated tube 80 with respect to the tumor C can be fixed. Therefore, a sharp needle tip 81 does not have to be formed at the distal portion of the elongated tube 80. Note that, when the elongated tube 80 comes into contact with the tumor C, it can be preferable that the elongated tube 80 bites or digs into the tumor C to some extent, even if the tumor C is not punctured. When the elongated tube 80 is not punctured by the tumor C, the tumor C can be prevented from scattering to other sites.

When it is determined that the tumor cells have been sufficiently killed, when it is determined that further irradiation is not desirable, or when a predetermined time has elapsed, the operator stops the irradiation with the second near-infrared ray and stops monitoring by the measurement device 50. Next, the operator removes the elongated tube 80 together with the optical fiber 41 and the measurement device 50 from the skin. Thereafter, the operator specifies the position of the tumor C that has been irradiated with the first near-infrared ray and the second near-infrared ray and leaves the record.

As a modification example of the elongated tube 80, the distal portion of the elongated tube 80 may have a light-transmitting portion formed of a transparent material that can transmit near-infrared rays. In this case, the optical fiber 41 may not protrude from the needle tip 81. The optical fiber 41 can irradiate at least one of the tumor C, the vicinity of the tumor C, or the regional lymph node with the first near-infrared ray and/or the second near-infrared ray from the inside of the elongated tube 80 through the elongated tube 80. Further, the measurement device 50 can measure the temperature or hardness of the tumor C through a transparent elongated tube 80 in a non-contact manner. Note that, the light-transmitting portion is preferably provided only at the distal portion of the elongated tube 80. By providing the light-transmitting portion only at the distal portion of the elongated tube 80, it becomes possible to prevent places other than the tumor C from being irradiated with near-infrared rays.

Figure 6A:
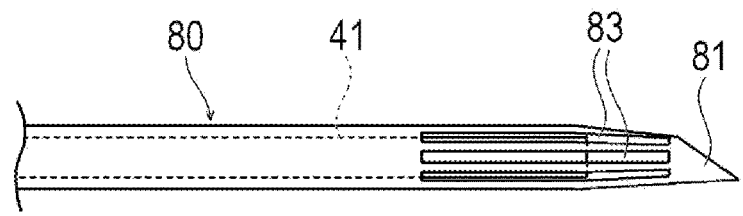
FIGS. 6A and 6B are plan views showing a modification example of the treatment system, where

Further, at least one slit 83 may be formed at the distal portion of the elongated tube 80 as in another modification example shown in FIG. 6A. The number and shape of the slits 83 are not particularly limited. In this case, the optical fiber 41 may not protrude from the needle tip 81. The optical fiber 41 can irradiate at least one of the tumor C, the vicinity of the tumor C, or the regional lymph node with the first near-infrared ray and/or the second near-infrared ray from the inside of the elongated tube 80 through the slit 83. Further, the measurement device 50 can measure the temperature or hardness of the tumor C through the slit 83 in a non-contact manner. Note that, the slit 83 is preferably provided only at the distal portion of the elongated tube 80. By providing the slit 83 only at the distal portion of the elongated tube 80, it becomes possible to prevent places other than the tumor C from being irradiated with near-infrared rays.

Figure 6B:
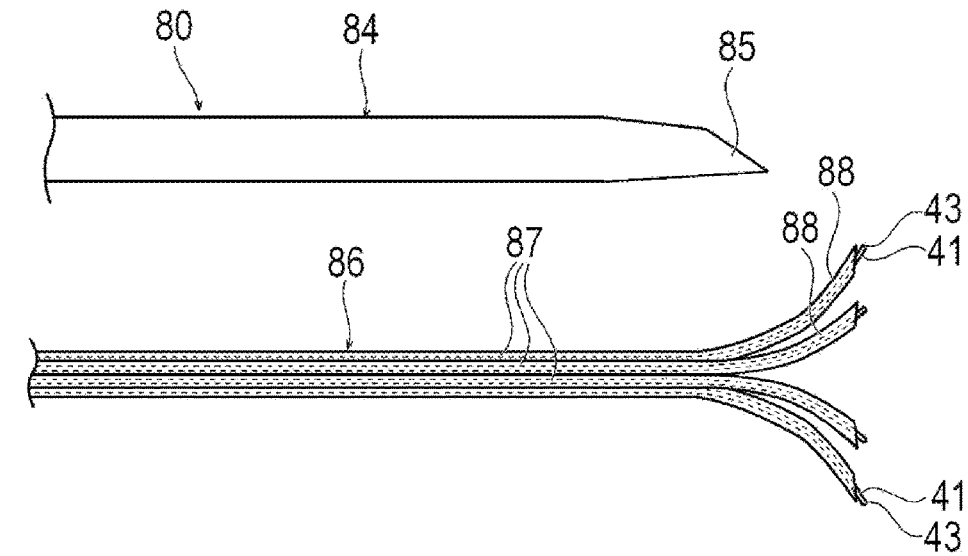

Further, the elongated tube 80 includes a hollow outer needle 84 having an outer needle tip 85 at the distal end and an inner needle 86 that can be inserted into the inside of the outer needle 84, as in another modification example shown in FIG. 6B. The inner needle 86 has a plurality of hollow branch needles 87 whose distal portion extends in the distal end direction. The plurality of branch needles 87 is preferably fixed as a bundle except for the widened distal portion. The branch needle 87 can be elastically deformable. The number of branch needles 87 is not particularly limited but can be preferably two or more. A sharp inner needle tip 88 is formed at the distal end of each branch needle 87. When the elongated tube 80 has a plurality of branch needles 87, it is preferable that a plurality of the optical fibers 41 is provided so as to be inserted into the respective branch needles 87.

Figure 9A:
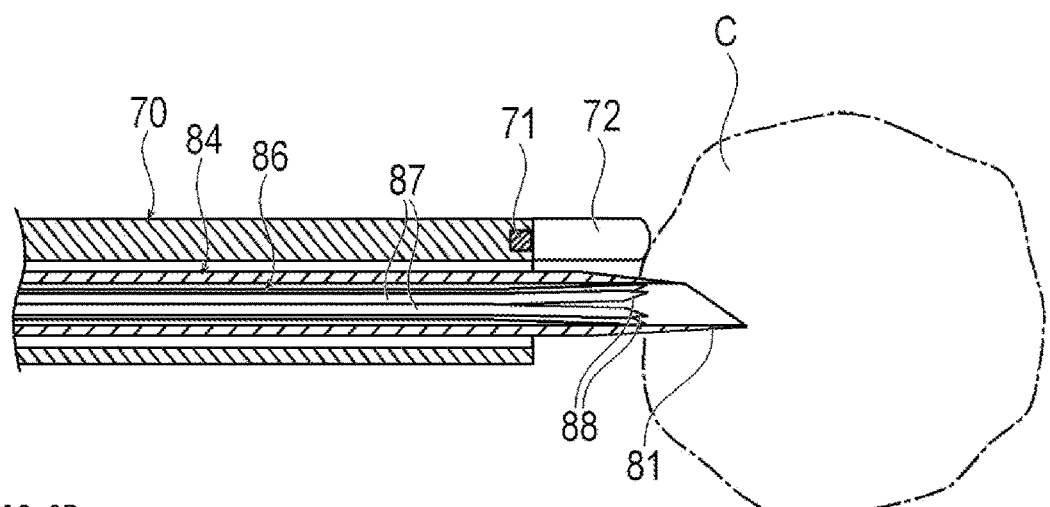
FIGS. 9A and 9B are cross-sectional views showing when the stomach cancer is treated using an elongated tube according to a modification example, where
Figure 9B:
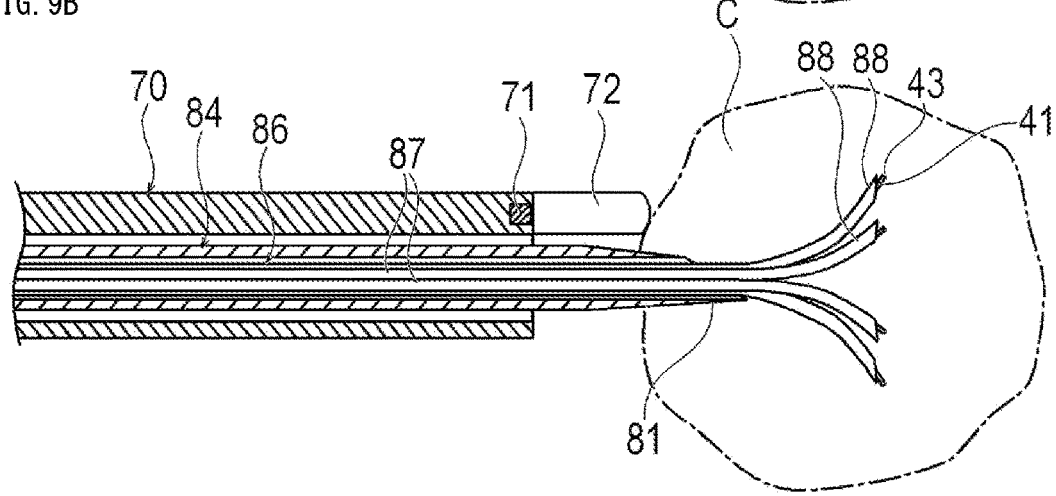

When the elongated tube 80 has the outer needle 84 and the inner needle 86, the operator punctures the tumor C with the outer needle 84 in a state where the inner needle 86 is accommodated in the outer needle 84 as shown in FIG. 9A. Thereafter, the operator can make the inner needle 86 to protrude from the outer needle 84 as shown in FIG. 9B. Thereby, the inner needle 86 spreads inside the tumor C. Thereafter, the optical fiber 41 is inserted into each branch needle 87, and the first near-infrared ray and the second near-infrared ray are emitted from each branch needle 87. For this reason, the plurality of optical fibers 41 can efficiently irradiate the entire tumor C with the first near-infrared ray and the second near-infrared ray. Note that, the optical fiber 41 may be fixedly disposed in each branch needle 87.

As described above, the treatment method according to the third embodiment is a treatment method for killing a tumor cell, the method including inserting the endoscope 70 from a mouth, a nose, or an anus and bringing the endoscope 70 to the vicinity of the tumor C having the tumor cell reachable from the mouth, the nose, or the anus, protruding the tubular elongated tube 80 in which the lumen 82 is formed from the endoscope 70, bringing the elongated tube 80 into contact with the tumor C or puncturing the tumor C with the elongated tube 80 while checking a camera image and/or an ultrasound image obtained from the endoscope 70, bringing the optical fiber 41 inserted into the lumen 82 of the elongated tube 80 into the tumor C or the vicinity of the tumor C, administering the antibody-photosensitive substance into a vein before the bringing of the endoscope 70 to the vicinity of the tumor C, irradiating at least one of the tumor C, the vicinity of the tumor C, or the regional lymph node with the first near-infrared ray by the optical fiber 41, and irradiating the antibody-photosensitive substance bound to a tumor cell membrane in the tumor cell with the second near-infrared ray having a shorter wavelength than that of the first near-infrared ray.

With the treatment method having the above-described configuration, at least one of the tumor C, the vicinity of the tumor C, or the regional lymph node can be effectively irradiated with the first near-infrared ray by the optical fiber 41 disposed in or near the tumor C via the endoscope 70. For this reason, more antigen-presenting cells can be gathered at the irradiation target site, and when the tumor cells are damaged and release the antigen, antigen presentation can be rather efficiently performed by more antigen-presenting cells, leading to T cell activation. Further, the optical fiber 41 inserted in the tumor C or in the vicinity of the tumor C can irradiate the antibody-photosensitive substance bound to the tumor cells with the near-infrared rays. For this reason, the photosensitivity of the antibody-photosensitive substance causes a chemical reaction to damage tumor cells and release the antigen. Therefore, since the antigen can be released in a state where more antigen-presenting cells are gathered in the tumor, the antigen can be efficiently presented by more antigen-presenting cells, leading to T cell activation. As a result, the present treatment method can improve or recover attack capability of immunity against cancer. Therefore, the present treatment method can enhance the effect of killing a tumor cell. Further, since it is not necessary to administer an adjuvant to activate the antigen-presenting cells, it is possible to reduce the relative burden on the patient such as side effects of the adjuvant.

Fourth Embodiment

Similar to the treatment method according to the third embodiment, the treatment method according to a fourth embodiment is applied to cancer treatment of an organ that can be reached from the mouth, nose, or anus. The treatment method according to the fourth embodiment can be suitably used for the treatment of, for example, pancreatic cancer, lung cancer, stomach cancer, duodenal cancer, esophageal cancer, colon cancer, and the like. Note that, the treatment method according to the fourth embodiment is different from the third embodiment in that the antibody-photosensitive substance is not administered intravenously but locally in the tumor C or in the vicinity of the tumor C. Note that, the treatment system is the same as the treatment system 60 used in the treatment method according to the third embodiment.

In the treatment method according to the fourth embodiment, the operator inserts the endoscope 70 from the mouth, nose, or anus without intravenous administration of the antibody-photosensitive substance, and causes the endoscope 70 to reach the vicinity of the tumor C. Next, the operator inserts the elongated tube 80 into the proximal portion of the endoscope 70 and causes the elongated tube 80 to protrude from the distal portion of the endoscope 70. Next, the operator punctures the tumor C with the needle tip 81 of the elongated tube 80 while checking the camera image and/or ultrasound image of the endoscope 70. Thereby, the position of the elongated tube 80 can be fixed with respect to the tumor C.

Next, the operator locally administers the antibody-photosensitive substance from the proximal side of the elongated tube 80 into the tumor C through the lumen 82. After local administration of the antibody-photosensitive substance into the tumor C, the operator waits until the antibody-photosensitive substance binds to the target cell membrane. When the antibody-photosensitive substance is locally administered to the tumor C to be treated, the time until the antibody-photosensitive substance binds to the target cell membrane is much shorter than that for intravenous administration, and is considered to be, for example, about 5 minutes to 10 minutes.

Next, the operator inserts the optical fiber 41 and the measurement device 50 from the proximal side of the lumen 82 of the elongated tube 80. Thereafter, similarly to the treatment method according to the third embodiment, the first infrared ray and second infrared ray are emitted using the optical fiber 41. Note that, since the subsequent procedure is the same as the treatment method according to the third embodiment, the description of the subsequent procedure is omitted. The irradiation with the second near-infrared ray is not particularly limited but is started, for example, about 5 minutes to 10 minutes after the local administration of the antibody-photosensitive substance.

As described above, the treatment method according to the fourth embodiment is a treatment method for killing a tumor cell, the method including inserting the endoscope 70 from a mouth, a nose, or an anus and bringing the endoscope 70 to the vicinity of the tumor C having the tumor cell reachable from the mouth, the nose, or the anus, protruding the tubular elongated tube 80 in which the lumen 82 is formed from the endoscope 70, bringing the elongated tube 80 into contact with the tumor C or puncturing the tumor C with the elongated tube 80 while checking a camera image and/or an ultrasound image obtained from the endoscope 70, bringing the optical fiber 41 inserted into the lumen 82 of the elongated tube 80 into the tumor C or the vicinity of the tumor C, administering the antibody-photosensitive substance into the tumor C or the vicinity of the tumor C from the elongated tube 80 after the bringing of the elongated tube 80 into contact with the tumor C or puncturing the tumor C with the elongated tube 80, irradiating at least one of the tumor C, the vicinity of the tumor C, or the regional lymph node with the first near-infrared ray by the optical fiber 41, and irradiating the antibody-photosensitive substance bound to a tumor cell membrane in the tumor cell with the second near-infrared ray having a shorter wavelength than that of the first near-infrared ray.

With the treatment method having the above-described configuration, at least one of the tumor C, the vicinity of the tumor C, or the regional lymph node can be effectively irradiated with the first near-infrared ray by the optical fiber 41 disposed in or near the tumor C via the endoscope 70. For this reason, more antigen-presenting cells can be gathered at the irradiation target site, and when the tumor cells are damaged and release the antigen, antigen presentation is efficiently performed by more antigen-presenting cells, leading to T cell activation. Further, as a method of damaging tumor cells and releasing antigen, the optical fiber 41 inserted into the tumor C or in the vicinity of the tumor C can irradiate the antibody-photosensitive substance bound to the tumor cells with the near-infrared rays. For this reason, the photosensitive substance of the antibody-photosensitive substance can cause a chemical reaction and damage the tumor cells. Therefore, when antigens are released from damaged tumor cells, the antigens are efficiently presented by a relatively larger number of antigen-presenting cells, leading to T cell activation. As a result, the present treatment method can improve or recover attack capability of immunity against cancer. Further, since there is no need to administer an adjuvant in order to activate the antigen-presenting cells, it is possible to reduce the relative burden on a patient due to side effects of the adjuvant. Furthermore, since the antibody-photosensitive substance is locally administered, the antibody-photosensitive substance can act on tumor cells in a relatively short time and efficiently. In addition, since the antibody-photosensitive substance can be administered in a relatively small amount only at a necessary place, the relative burden on the patient can be reduced.

Fifth Embodiment

The treatment method according to a fifth embodiment is applied to cancer treatment of organs that can be reached percutaneously. The treatment method according to the fifth embodiment can be suitably used for the treatment of, for example, breast cancer, liver cancer, skin cancer, head and neck cancer, and the like.

Figure 10:
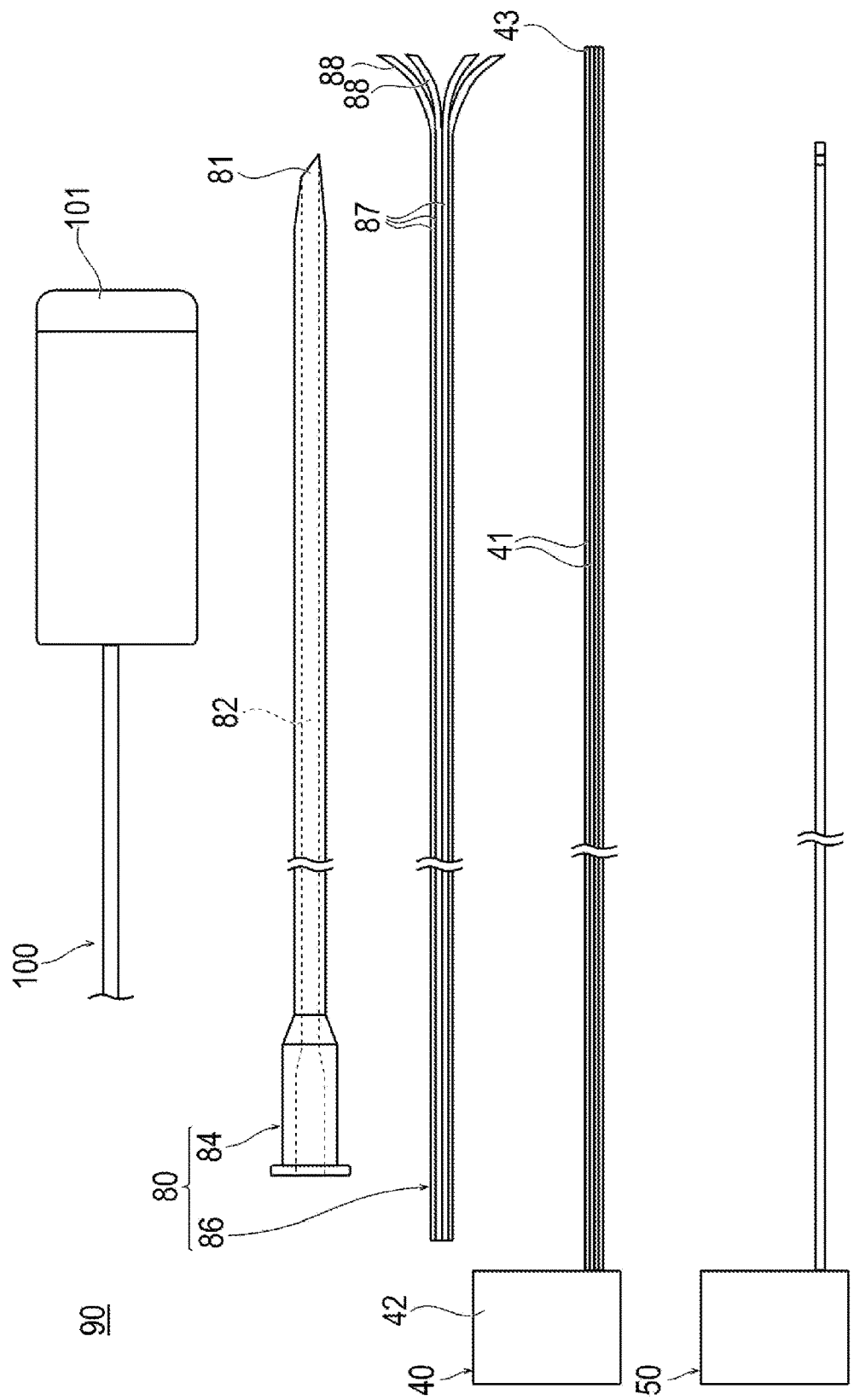
FIG. 10 is a plan view showing a treatment system used in a treatment method according to a fifth embodiment.

In the treatment method according to the fifth embodiment, as shown in FIG. 10, a treatment system 90 that can be punctured percutaneously and inserted into the body is used to emit the first near-infrared ray and the second near-infrared ray. The treatment system 90 includes the elongated tube 80 having the outer needle 84 and the inner needle 86, the light irradiation device 40 that can be inserted into the elongated tube 80, the measurement device 50 that can be inserted into the elongated tube 80, and an ultrasound diagnostic device 100.

The elongated tube 80 is the elongated tube 80 shown in FIG. 6B as a modification example of the third embodiment, and includes the outer needle 84 and the inner needle 86. The ultrasound diagnostic device 100 is a known device that can acquire an ultrasound image. The ultrasound diagnostic device 100 includes a probe 101 that transmits and receives ultrasound waves. The light irradiation device 40 includes the plurality of optical fibers 41 corresponding to the number of branch needles 87 of the inner needle 86. Each optical fiber 41 can be inserted into the branch needle 87. Alternatively, the optical fiber 41 may be fixed inside the branch needle 87.

Next, the treatment method according to the fifth embodiment will be described taking the case of treating breast cancer as an example. Note that, this description is not intended to limit the organs to be treated.

Figure 11:
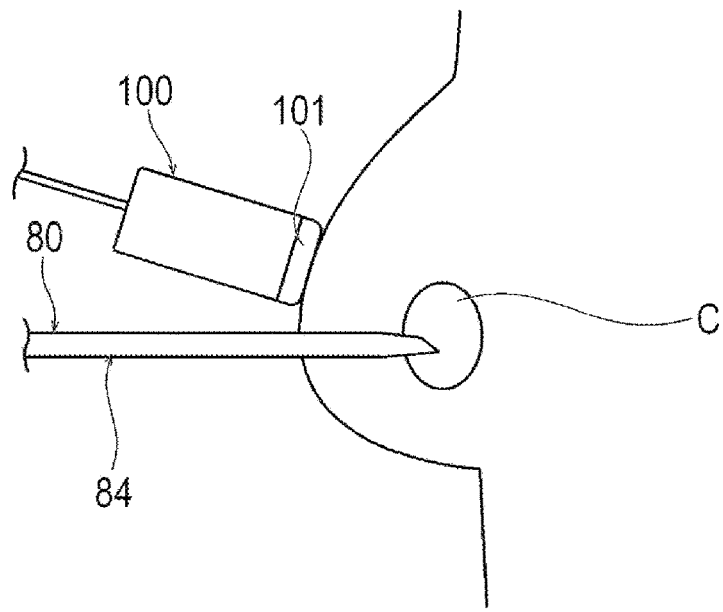
FIG. 11 is a schematic view showing a state inside a body when treating breast cancer by the treatment method according to the fifth embodiment.
Figure 12A:
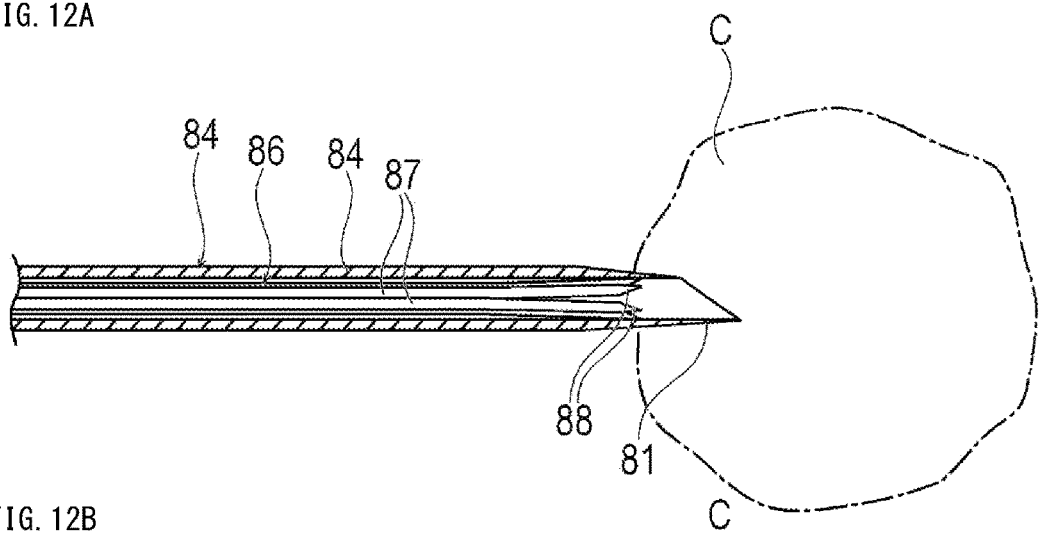
FIGS. 12A and 12B are cross-sectional views showing when the breast cancer is treated using the treatment system, where
Figure 12B:
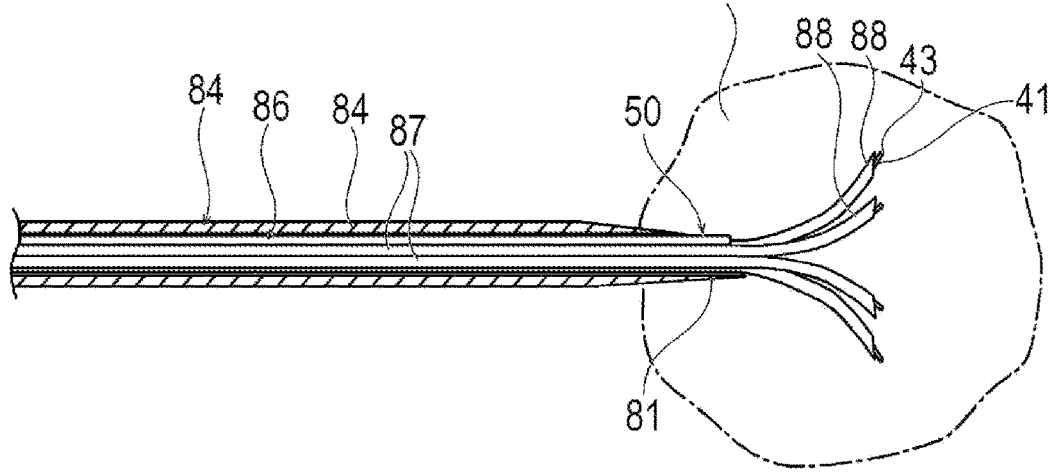

First, the operator administers the antibody-photosensitive substance intravenously. In accordance with an exemplary embodiment, for example, after about 12 hours to 36 hours from intravenous administration, the operator brings the probe 101 of the ultrasound diagnostic device 100 into contact with the skin, as shown in FIG. 11. Next, while checking the ultrasound image, the operator punctures the tumor C from the skin located in the vicinity of the tumor C with the outer needle 84 accommodating the inner needle 86 whose inner needle tip 88 is elastically deformed as shown in FIG. 12A. Note that, the outer needle 84 may be punctured not in the tumor C but in the vicinity of the tumor C. After the operator punctures the tumor C or the vicinity of the tumor C with the outer needle 84, the operator protrudes the inner needle 86 from the outer needle 84 toward the distal side as shown in FIG. 12B. Thereby, the inner needle 86 spreads at the inside of the tumor C or the vicinity of the tumor C. Thereby, the position of the inner needle 86 is fixed with respect to the tumor C. At this time, it is preferable that at least one of the plurality of branch needles 87 is punctured into the tumor C, and more preferably, all the branch needles 87 are punctured into the tumor C. Note that, it is possible that all the branch needles 87 are punctured into the vicinity of the tumor C instead of the tumor C.

Next, the operator inserts the optical fiber 41 into each branch needle 87. The irradiation unit 43 of each optical fiber 41 protrudes from the branch needle 87. Thereby, the operator can emit the first near-infrared ray and the second near-infrared ray from the optical fiber 41 inserted into each branch needle 87. For this reason, the plurality of optical fibers 41 can efficiently irradiate the entire tumor C with the first near-infrared ray and the second near-infrared ray. Note that, the optical fiber 41 may not protrude from the branch needle 87. Further, the optical fiber 41 and/or the measurement device 50 may be disposed in advance in the branch needle 87 before puncturing.

The distal portion of the branch needle 87 may have a light-transmitting portion formed of a transparent material that transmits near-infrared rays. Thereby, the optical fiber 41 may not protrude from the branch needle 87. The optical fiber 41 can irradiate at least one of the tumor C, the vicinity of the tumor C, or the regional lymph node with near-infrared rays from the inside of the branch needle 87 through the branch needle 87. Note that, the light-transmitting portion is preferably provided only at the distal portion of the branch needle 87. By configuring in this way, it becomes possible to prevent places other than the tumor C from being irradiated with near-infrared rays.

Further, the distal portion of the branch needle 87 may have a slit. Thereby, the optical fiber 41 may not protrude from the branch needle 87. The optical fiber 41 can irradiate at least one of the tumor C, the vicinity of the tumor C, or the regional lymph node with the near-infrared rays from the inside of the branch needle 87 through a slit. Note that, the slit is preferably provided only at the distal portion of the branch needle 87. By configuring in this way, it becomes possible to prevent places other than the tumor C from being irradiated with near-infrared rays.

Next, the operator inserts the measurement device 50 from the proximal side of the lumen 82 of the outer needle 84 of the elongated tube 80. The distal portion of the measurement device 50 protrudes from the outer needle 84 toward the distal side at the inside the hole formed in the tumor C by the outer needle 84.

Next, the operator performs irradiation of at least one of the tumor C, the vicinity of the tumor C, or the regional lymph node with the first near-infrared ray from the optical fiber 41. Thereby, when more antigen-presenting cells can be gathered at the irradiation target site, the tumor cells are damaged and the antigen is released, antigen presentation is efficiently performed by more antigen-presenting cells, leading to T cell activation. For this reason, the attack capability of immunity against cancer can be improved or recovered. The operator stops the irradiation with the first near-infrared ray after a predetermined time has elapsed since the start of the irradiation with the first near-infrared ray.

Next, the operator measures the temperature or hardness of the tumor C with the measurement device 50 while irradiating with the second near-infrared ray from the plurality of optical fibers 41. By continuing the measurement of tumor C, it is possible to monitor in real time that the target cell to which the antibody-photosensitive substance is bound is irradiated with the second near-infrared ray. The irradiation with the second near-infrared ray starts, for example, 12 hours to 36 hours after intravenous administration.

The irradiation direction of near-infrared rays from the optical fiber 41 is appropriately selected. For example, the irradiation direction of the near-infrared rays may be the distal end direction of the optical fiber 41, the direction orthogonal to the axial direction of the optical fiber 41, or all directions (i.e., the distal end direction, the direction orthogonal to the axial direction, and the directions between the distal end direction and the direction orthogonal to the axial direction). The operator can appropriately select the optical fiber to be used according to the near-infrared ray irradiation target site.

The operator continues the irradiation with the second near-infrared ray while checking the death of the tumor cells by the irradiation with the second near-infrared ray by monitoring with the measurement device 50. When it is determined that the tumor cells have been sufficiently killed, when it is determined that further irradiation is not desirable, or when a predetermined time has elapsed, the operator stops the irradiation with the second near-infrared ray and stops monitoring by the measurement device 50. Next, the operator pulls the inner needle 86 toward the proximal side and accommodates the inner needle 86 in the outer needle 84. Thereby, the branch needle 87 is accommodated in the outer needle 84 while being deformed linearly. Next, the operator removes the outer needle 84 together with the inner needle 86, the optical fiber 41, and the measurement device 50 from the skin. Thereafter, the operator specifies the position of the tumor C that has been irradiated with the first near-infrared ray and the second near-infrared ray and leaves the record.

The monitoring of the irradiation with the second near-infrared ray may be performed by the optical fiber 41 for near-infrared ray irradiation. Since a plurality of optical fibers 41 is provided, the temperature can be measured by each optical fiber 41. Therefore, according to the temperature measured by each optical fiber 41, the irradiation with the second near-infrared ray from each optical fiber 41 can be controlled separately. The measurement device 50 may be a temperature measurement device using a thermocouple or a hardness measurement device using ultrasound waves. Further, the monitoring of the irradiation with the second near-infrared ray may be performed by a sensor disposed outside the body or a sensor inserted in a lumen in a living body.

As described above, the treatment method according to the fifth embodiment is a treatment method for killing a tumor cell, the method including puncturing the tumor C having the tumor cell or the vicinity of the tumor C percutaneously with the hollow branch needle 87 while acquiring and checking an ultrasound image percutaneously, inserting the optical fiber 41 into a lumen of the branch needle 87 and bringing the optical fiber 41 into the tumor C or the vicinity of the tumor C, administering the antibody-photosensitive substance into a vein before the bringing of the branch needle 87 to the vicinity of the tumor C, irradiating at least one of the tumor C, the vicinity of the tumor C, or the regional lymph node with the first near-infrared ray from the optical fiber 41, and irradiating the antibody-photosensitive substance bound to a tumor cell membrane in the tumor cell with the second near-infrared ray having a shorter wavelength than that of the first near-infrared ray.

With the treatment method having the above-described configuration, at least one of the tumor C, the vicinity of the tumor C, or the regional lymph node can be effectively irradiated with the first near-infrared ray by the optical fiber 41 disposed in or near the tumor C via the branch needle 87. For this reason, more antigen-presenting cells can be gathered at the irradiation target site, and when the tumor cells are damaged and release the antigen, antigen presentation can be efficiently performed by more antigen-presenting cells, leading to T cell activation. Further, as a method of damaging tumor cells, the optical fiber 41 inserted into the tumor C or in the vicinity of the tumor C can effectively irradiate the antibody-photosensitive substance bound to the tumor cells with the second near-infrared ray. Thereby, the photosensitive substance of the antibody-photosensitive substance can cause a chemical reaction and kill the tumor cells. As a result, the antigen is released from the dead tumor cell in a state where more antigen-presenting cells are gathered, and the antigen presentation is efficiently performed. As a result, the present treatment method can improve or recover attack capability of immunity against cancer. Further, since it is not necessary to administer an adjuvant to activate the antigen-presenting cells, the relative burden on the patient can be reduced.

Note that, in the fifth embodiment, the inner needle 86 having the branch needle 87 may not be used. In this case, the optical fiber 41 can be inserted into the lumen 82 of the outer needle 84.

Sixth Embodiment

Similar to the treatment method according to the fifth embodiment, the treatment method according to a sixth embodiment is applied to cancer treatment of an organ that can be reached percutaneously. The treatment method according to the sixth embodiment can be suitably used for the treatment of, for example, breast cancer, liver cancer, skin cancer, head and neck cancer, and the like. Note that, the treatment method according to the sixth embodiment is different from the fifth embodiment in that the antibody-photosensitive substance is not administered intravenously but locally in the tumor C or in the vicinity of the tumor C by the branch needle 87 of the elongated tube 80. Note that, the treatment device is the same as the device used in the treatment method according to the fifth embodiment.

In the treatment method according to the sixth embodiment, the operator punctures the outer needle 84 of the elongated tube 80 from the skin located in the vicinity of the tumor C to the tumor C or in the vicinity of the tumor C while checking the ultrasound image without intravenous administration of the antibody-photosensitive substance. The operator can protrude the inner needle 86 from the outer needle 84 after puncturing the outer needle 84. Thereby, the inner needle 86 expands inside the tumor C or the vicinity of the tumor C. Thereby, the position of the inner needle 86 is fixed with respect to the tumor C.

Next, the operator locally administers the antibody-photosensitive substance from the proximal side of the inner needle 86 through the inside of the inner needle 86 into the tumor C or the vicinity of the tumor C. After local administration of the antibody-photosensitive substance, the operator waits until the antibody-photosensitive substance binds to the target cell membrane. When the antibody-photosensitive substance is locally administered to the tumor C to be treated, the time until the antibody-photosensitive substance binds to the target cell membrane is much shorter than that for intravenous administration, and is considered to be, for example, about 5 minutes to 10 minutes.

Next, the operator inserts the optical fiber 41 into each branch needle 87. Thereafter, similarly to the treatment method according to the fifth embodiment, the first infrared ray and second infrared ray are emitted using the optical fiber 41. Note that, since the subsequent procedure is the same as the treatment method according to the fifth embodiment, the description of the subsequent procedure is omitted. The irradiation with the second near-infrared ray is not particularly limited but is started, for example, about 5 minutes to 10 minutes after the local administration of the antibody-photosensitive substance.

As described above, the treatment method according to the sixth embodiment is a treatment method for killing a tumor cell, the method including puncturing the tumor C having the tumor cell or the vicinity of the tumor C percutaneously with the hollow elongated tube 80 while acquiring and checking an ultrasound image percutaneously, bringing the optical fiber 41 inserted into a lumen of the branch needle 87 into the tumor C or the vicinity of the tumor C, administering the antibody-photosensitive substance into the tumor C or the vicinity of the tumor C from the branch needle 87 after the bringing of the branch needle 87 to the vicinity of the tumor C, irradiating at least one of the tumor C, the vicinity of the tumor C, or the regional lymph node with the first near-infrared ray by the optical fiber 41, and irradiating the antibody-photosensitive substance bound to a tumor cell membrane in the tumor cell with the second near-infrared ray having a shorter wavelength than that of the first near-infrared ray.

With the treatment method having the above-described configuration, at least one of the tumor C, the vicinity of the tumor C, or the regional lymph node can be effectively irradiated with the first near-infrared ray by the optical fiber 41 disposed in or near the tumor C via the branch needle 87. For this reason, more antigen-presenting cells can be gathered at the irradiation target site, and when the tumor cells are damaged and release the antigen, antigen presentation is efficiently performed by more antigen-presenting cells, leading to T cell activation. Further, the optical fiber 41 inserted in the tumor C or in the vicinity of the tumor C can effectively irradiate the antibody-photosensitive substance bound to the tumor cells with the second near-infrared ray. Thereby, the photosensitive substance of the antibody-photosensitive substance can cause a chemical reaction and kill the tumor cells. Therefore, the antigen is released from the dead tumor cell in a state where more antigen-presenting cells are gathered, and the antigen presentation is efficiently performed. As a result, the present treatment method can improve or recover attack capability of immunity against cancer and enhance the effect of killing tumor cells. Further, since there is no need to administer an adjuvant in order to activate the antigen-presenting cells, the burden on a patient due to side effects of the adjuvant can be reduced. Furthermore, since the antibody-photosensitive substance is locally administered, the antibody-photosensitive substance can act on tumor cells in a relatively short time with relatively high probability. In addition, since the antibody-photosensitive substance can be administered in a small amount only at a necessary place, the relative burden on the patient can be reduced.

Seventh Embodiment

Similar to the treatment method according to the first embodiment, the treatment method according to a seventh embodiment is applied to cancer treatment of an organ that can be reached transvascularly. The treatment method according to the seventh embodiment can be suitably used, for example, for the treatment of liver cancer, lung cancer, pancreatic cancer, and the like. Note that, the treatment method according to the seventh embodiment is different from the first embodiment in that the antibody-photosensitive substance is not administered intravenously but the anti-cancer agent is administered locally or intravenously to the nutrient blood vessel of the organ where tumor C is formed. In the treatment method according to the seventh embodiment, the treatment system 10 (see FIG. 1) used in the treatment method according to the first embodiment can be used. Note that, the measurement device 50 for monitoring that the tumor cell to which the antibody-photosensitive substance is bound is irradiated with the second near-infrared ray may not be used.

The anti-cancer agent is not specifically limited, and for example, the anti-cancer agent can be doxorubicin, oxaliplatin, and the like.

Next, the treatment method according to the seventh embodiment will be described taking the case of treating liver cancer as an example. Note that, this description is not intended to limit the organs to be treated.

In the treatment method according to the seventh embodiment, the operator inserts the catheter 30 into the hepatic artery while leading the guide wire 20 from, for example, the femoral artery, brachial artery, radial artery, and the like as shown in FIG. 2. Next, the operator removes the guide wire 20 from the catheter 30.

Figure 13:
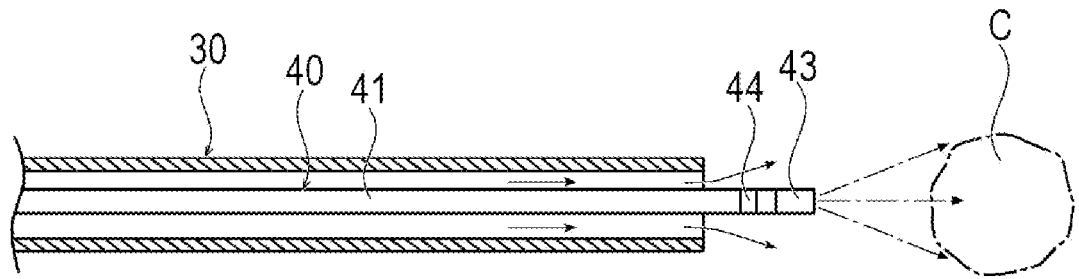
FIG. 13 is a cross-sectional view showing when treating with a treatment method according to a seventh embodiment.

Next, the operator inserts the optical fiber 41 into the lumen 31 from the proximal side of the catheter 30. As shown in FIG. 13, the distal portion of the optical fiber 41 protrudes from the catheter 30 toward the distal side. Next, the operator causes the position of the orientation marker 44 of the optical fiber 41 to reach the target position while checking the position of the orientation marker 44 of the optical fiber 41 under X-ray contrast. The target position is a position close to the tumor C and capable of irradiating at least one of the tumor C, the vicinity of the tumor C, or the regional lymph node with the first near-infrared ray.

Next, the operator supplies the saline solution to the lumen 31 from the proximal side of the catheter 30. The saline solution flows into the hepatic artery through a gap in the lumen 31 in which the optical fiber 41 is inserted. Thereby, the saline solution is injected (flushed) from the catheter 30 to the hepatic artery. For this reason, blood in the hepatic artery where the optical fiber 41 is located is pushed away (i.e., displaced by the saline solution), and the hepatic artery is temporarily filled with the saline solution. When the catheter 30 has the balloon 32, the balloon 32 may be inflated before, during, or after flushing the saline solution. Thereby, the blood flow in the hepatic artery is blocked and the hepatic artery is temporarily filled with the saline solution. For this reason, the hepatic artery can be more reliably filled with the saline solution. Note that, the operator may inflate the balloon 32 without flushing the saline solution.

After filling the hepatic artery with the saline solution or blocking the blood flow in the hepatic artery, the operator may observe the hepatic artery with the optical fiber 41. Thereby, the operator can accurately check that the hepatic artery is filled with the saline solution and/or that the blood flow in the hepatic artery is blocked.

Next, the operator performs irradiation of at least one of the tumor C, the vicinity of the tumor C, or the regional lymph node with the first near-infrared ray from the optical fiber 41 for photolaser adjuvant. At this time, since the hepatic artery is filled with the saline solution and/or the blood flow in the hepatic artery is blocked, the irradiation with the first near-infrared ray is hardly affected by blood. For this reason, the first near-infrared ray can effectively reach at least one of the tumor C, the vicinity of the tumor C, or the regional lymph node. Therefore, the irradiation with the first near-infrared ray can be performed rather effectively. Thereby, more antigen-presenting cells can be gathered at the irradiation target site, and when the tumor cells are damaged and release the antigen, antigen presentation is efficiently performed by more antigen-presenting cells, leading to T cell activation. For this reason, the attack capability of immunity against cancer can be improved or recovered. The operator stops the irradiation with the first near-infrared ray after a predetermined time has elapsed since the start of the irradiation with the first near-infrared ray.

Next, the operator removes the optical fiber 41 from the catheter 30. Next, the operator locally administers the anti-cancer agent from the proximal side of the catheter 30 into the hepatic artery via the lumen 31. Note that, in the case of treatment of lung cancer, an anti-cancer agent is locally administered to the bronchial artery, which is the nutrient artery of the lung to be treated. Note that, without removing the optical fiber 41 from the catheter 30, an anti-cancer agent may be administered through the gap between the lumen 31 and the optical fiber 41. Alternatively, the operator may administer the anti-cancer agent intravenously. The administration of the anti-cancer agent may be performed before the irradiation with the first near-infrared ray by the optical fiber 41. Therefore, administration of anti-cancer agent may be performed before inserting the optical fiber 41 into the catheter 30. The operator removes the catheter 30 together with the optical fiber 41 from the skin. The operator specifies the position of the tumor C that has been irradiated with the first near-infrared ray and leaves the record.

As described above, the treatment method according to the seventh embodiment is a treatment method for killing a tumor cell, the method including inserting the catheter 30 into the main artery of an organ having the tumor cell, inserting the optical fiber 41 into the catheter 30, reducing an influence of blood in the artery on the near-infrared ray, irradiating at least one of the tumor C having the tumor cell, the vicinity of the tumor C, or the regional lymph node with the first near-infrared ray from the optical fiber 41, and administering the anti-cancer agent into a vein or administering the anti-cancer agent into an artery from the catheter 30.

With the treatment method having the above-described configuration, it is possible to effectively irradiate at least one of the tumor C, the vicinity of the tumor C, or a regional lymph node with the first near-infrared ray from the optical fiber 41 inserted into an artery near the tumor C through the catheter 30. For this reason, more antigen-presenting cells can be gathered at an irradiation target site, and when tumor cells are damaged and release the antigen, antigen presentation is performed efficiently, leading to T cell activation. Further, as a method of damaging tumor cells, this treatment method can administer an anti-cancer agent intravenously or locally to an artery. Therefore, in the present treatment method, the antigen is released from the tumor cells in a state where the antigen-presenting cells are gathered in the vicinity of the tumor, so that the antigen is efficiently presented. As a result, the present treatment method can improve or recover attack capability of immunity against cancer. Further, since it is not necessary to administer an adjuvant to activate the antigen-presenting cells, the relative burden on the patient such as side effects of the adjuvant can be reduced. When the anti-cancer agent is locally administered, the anti-cancer agent can be allowed to act on tumor cells in a relatively short time and relatively efficiently. Further, since the anti-cancer agent can be administered in a relatively small amount only at a necessary place, the relative burden on the patient can be reduced.

Eighth Embodiment

Similar to the treatment method according to the third embodiment, the treatment method according to an eighth embodiment is applied to cancer treatment of an organ that can be reached from the mouth, nose, or anus. The treatment method according to the eighth embodiment can be suitably used for the treatment of, for example, pancreatic cancer, lung cancer, stomach cancer, duodenal cancer, esophageal cancer, colon cancer, and the like. Note that, the treatment method according to the eighth embodiment is different from the third embodiment in that the antibody-photosensitive substance is not administered intravenously, but the anti-cancer agent is administered locally in the tumor C or in the vicinity of the tumor C. In the treatment method according to the eighth embodiment, the treatment system 60 (see FIG. 5) used in the treatment method according to the third embodiment can be used. Note that, the measurement device 50 for monitoring may not be used.

Next, the treatment method according to the eighth embodiment will be described taking the case of treating stomach cancer as an example. Note that, this description is not intended to limit the organs to be treated.

Figure 14:
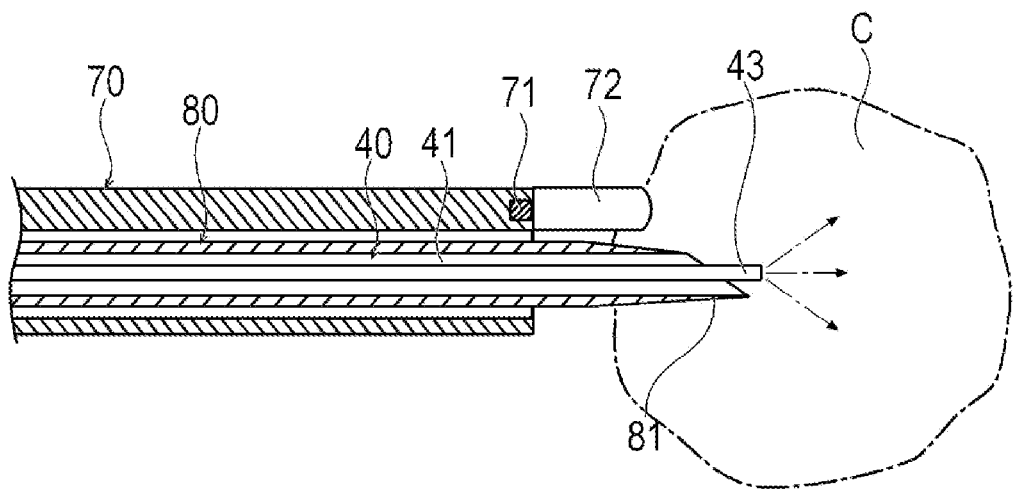
FIG. 14 is a cross-sectional view showing when treating with a treatment method according to an eighth embodiment.

The operator inserts the endoscope 70 from the mouth or nose as shown in FIG. 7 so that the endoscope 70 reaches the vicinity of the stomach cancer. Next, the operator inserts the elongated tube 80 into the proximal portion of the endoscope 70 and causes the elongated tube 80 to protrude from the distal portion of the endoscope 70. Next, as shown in FIG. 14, the operator causes the needle tip 81 of the elongated tube 80 to come into contact with and puncture the tumor C while checking the camera image and/or ultrasound image of the endoscope 70. Thereby, the position of the elongated tube 80 is fixed with respect to the tumor C.

Next, the operator inserts the optical fiber 41 from the proximal side of the lumen 82 of the elongated tube 80. The distal portion of the optical fiber 41 protrudes from the needle tip 81 toward the distal side inside the hole formed in the tumor C by the needle tip 81. Note that, the optical fiber 41 and the measurement device 50 do not have to protrude from the needle tip 81.

Next, the operator performs irradiation of at least one of the tumor C, the vicinity of the tumor C, or the regional lymph node with the first near-infrared ray from the optical fiber 41. Thereby, more antigen-presenting cells can be gathered at an irradiation target site, and when tumor cells are damaged and release the antigen, antigen presentation is performed efficiently, leading to T cell activation. For this reason, the attack capability of immunity against cancer can be improved or recovered. The operator stops the irradiation with the first near-infrared ray after a predetermined time has elapsed since the start of the irradiation with the first near-infrared ray.

Next, the operator removes the optical fiber 41 from the elongated tube 80. Next, the operator locally administers the anti-cancer agent from the proximal side of the catheter 30 into the tumor C or the vicinity of the tumor C via the lumen 31. Note that, without removing the optical fiber 41 from the elongated tube 80, an anti-cancer agent may be administered through the gap between the lumen 82 and the optical fiber 41. Alternatively, the operator may administer the anti-cancer agent intravenously. The administration of the anti-cancer agent may be performed before the irradiation with the first near-infrared ray by the optical fiber 41. Therefore, administration of anti-cancer agent may be performed before inserting the optical fiber 41 into the elongated tube 80. The operator specifies the position of the tumor C that has been irradiated with the first near-infrared ray and leaves the record. Next, the operator collects the catheter 30 and the optical fiber 41 in the endoscope 70.

As described above, the treatment method according to the eighth embodiment is a treatment method for killing a tumor cell, the method including inserting the endoscope 70 from a mouth, a nose, or an anus and bringing the endoscope 70 to the vicinity of the tumor C having the tumor cell reachable from the mouth, the nose, or the anus, protruding the tubular elongated tube 80 in which the lumen 82 is formed from the endoscope 70, bringing the elongated tube 80 into contact with the tumor C or puncturing the tumor C with the elongated tube 80 while checking a camera image and/or an ultrasound image obtained by the endoscope 70, bringing the optical fiber 41 inserted into the lumen 82 of the elongated tube 80 into the tumor C or the vicinity of the tumor cell, irradiating at least one of the tumor C, the vicinity of the tumor C, or the regional lymph node with the first near-infrared ray by the optical fiber 41, and administering the anti-cancer agent to the vein or administering the anti-cancer agent to the tumor cell C or the vicinity of the tumor cell C from the elongated tube 80.

With the treatment method having the above-described configuration, at least one of the tumor C, the vicinity of the tumor C, or the regional lymph node can be effectively irradiated with the first near-infrared ray by the optical fiber 41 disposed in or near the tumor C via the endoscope 70. For this reason, more antigen-presenting cells can be gathered at an irradiation target site, and when tumor cells are damaged and release the antigen, antigen presentation is performed efficiently, leading to T cell activation. Further, in the present treatment method, the anti-cancer agent can be administered intravenously or locally as a method of damaging tumor cells. Therefore, since antigens are released from tumor cells in a state where antigen-presenting cells are gathered, antigens are presented by more antigen-presenting cells. As a result, the present treatment method can improve or recover attack capability of immunity against cancer. Further, since there is no need to administer an adjuvant in order to activate the antigen-presenting cells, the burden on a patient due to side effects of the adjuvant can be reduced. When the anti-cancer agent is locally administered, the anti-cancer agent can be allowed to act on tumor cells in a relatively short time with relatively higher efficiency. Further, since the anti-cancer agent can be administered in a small amount only at a necessary place, the relative burden on the patient can be reduced.

Ninth Embodiment

Similar to the treatment method according to the fifth embodiment, the treatment method according to a ninth embodiment is applied to cancer treatment of an organ that can be reached percutaneously. The treatment method according to the ninth embodiment can be suitably used for the treatment of, for example, breast cancer, liver cancer, skin cancer, head and neck cancer, and the like. Note that, the treatment method according to the ninth embodiment is different from the fifth embodiment in that the antibody-photosensitive substance is not administered intravenously, but the anti-cancer agent is administered locally in the tumor C or in the vicinity of the tumor C or administered intravenously. In the treatment method according to the ninth embodiment, the treatment system 90 (see FIG. 10) used in the treatment method according to the fifth embodiment can be used. Note that, the measurement device 50 for monitoring may not be used. Further, the elongated tube 80 may have a form having a plurality of branch needles 87 as shown in FIG. 10, but may have a form having a single needle tip 81 as shown in FIG. 5. Here, the elongated tube 80 will be described as having a single needle tip 81.

Next, the treatment method according to the ninth embodiment will be described taking the case of treating breast cancer as an example. Note that, this description is not intended to limit the organs to be treated.

Figure 15:
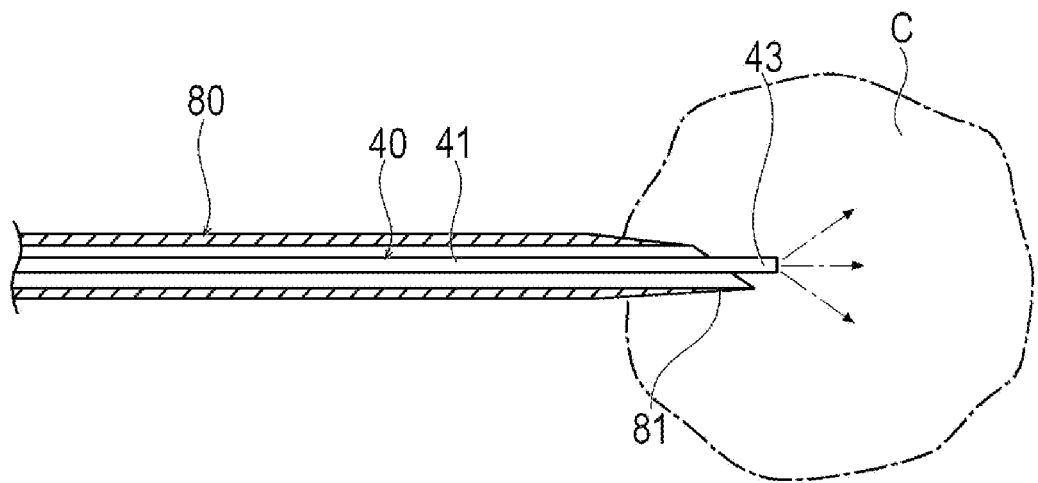
FIG. 15 is a cross-sectional view showing when treating with a treatment method according to a ninth embodiment.

The operator brings the probe 101 of the ultrasound diagnostic device 100 into contact with the skin, as shown in FIG. 11. Next, while checking the ultrasound image, the operator punctures the elongated tube 80 having the needle tip 81 from the skin located in the vicinity of the tumor C to the tumor C or the vicinity of the tumor C as shown in FIG. 15.

Next, the operator inserts the optical fiber 41 into the elongated tube 80. The irradiation unit 43 of the optical fiber 41 protrudes from the needle tip 81. Note that, the optical fiber 41 may not protrude from the needle tip 81.

The distal portion of the elongated tube 80 may be formed of a transparent material that transmits the first near-infrared ray. Thereby, the optical fiber 41 may not protrude from the needle tip 81. The optical fiber 41 can irradiate at least one of the tumor C, the vicinity of the tumor C, or the regional lymph node with the first near-infrared ray from the inside of the distal portion of the elongated tube 80 through the elongated tube 80.

Further, the distal portion of the elongated tube 80 may have a slit. Thereby, the optical fiber 41 may not protrude from the needle tip 81. The optical fiber 41 can irradiate at least one of the tumor C, the vicinity of the tumor C, or the regional lymph node with the first near-infrared ray from the inside of the distal portion of the elongated tube 80 through the slit.

Next, the operator performs irradiation of at least one of the tumor C, the vicinity of the tumor C, or the regional lymph node with the first near-infrared ray from the optical fiber 41. Thereby, more antigen-presenting cells can be gathered at the irradiation target site, and thereby, when the tumor cells are damaged and release the antigen, antigen presentation is efficiently performed, leading to T cell activation. For this reason, the attack capability of immunity against cancer is improved or recovered. The operator stops the irradiation with the first near-infrared ray after a predetermined time has elapsed since the start of the irradiation with the first near-infrared ray.

Next, the operator removes the optical fiber 41 from the elongated tube 80. Next, the operator locally administers the anti-cancer agent from the proximal side of the elongated tube 80 into the tumor C or the vicinity of the tumor C via the lumen 82. Note that, without removing the optical fiber 41 from the elongated tube 80, an anti-cancer agent may be administered through the gap between the lumen 82 and the optical fiber 41. Alternatively, the operator may administer the anti-cancer agent intravenously. The administration of the anti-cancer agent may be performed before the irradiation with the first near-infrared ray by the optical fiber 41. Therefore, administration of anti-cancer agent may be performed before inserting the optical fiber 41 into the elongated tube 80. Next, the operator removes the elongated tube 80 and the optical fiber 41 from the skin. The operator specifies the position of the tumor C that has been irradiated with the first near-infrared ray and leaves the record.

As described above, the treatment method according to the ninth embodiment is a treatment method for killing a tumor cell, the method including puncturing the tumor C having the tumor cell or the vicinity of the tumor C percutaneously with the hollow elongated tube 80 while acquiring and checking an ultrasound image percutaneously, bringing the optical fiber 41 inserted into the lumen 82 of the elongated tube 80 having the needle tip 81 into the tumor C or the vicinity of the tumor C, irradiating at least one of the tumor C, the vicinity of the tumor C, or the regional lymph node with the first near-infrared ray by the optical fiber 41, and administering the anti-cancer agent into the vein or to administering to the tumor C or the vicinity of the tumor C from the elongated tube 80.

With the treatment method having the above-described configuration, at least one of the tumor C, the vicinity of the tumor C, or the regional lymph node can be effectively irradiated with the first near-infrared ray by the optical fiber 41 disposed in or near the tumor C via the elongated tube 80 having the needle tip 81. For this reason, more antigen-presenting cells can be gathered at an irradiation target site, and when tumor cells are damaged and release the antigen, antigen presentation is performed efficiently, leading to T cell activation. Further, in the present treatment method, the anti-cancer agent can be administered intravenously or locally as a method of damaging tumor cells. Therefore, since antigens are released from tumor cells in a state where antigen-presenting cells are gathered, antigen presentation is efficiently performed by more antigen-presenting cells, and as a result, the present treatment method can improve or recover the attack capability of immunity against cancer. Therefore, the present treatment method can enhance the effect of killing a tumor cell. Further, since there is no need to administer an adjuvant in order to activate the antigen-presenting cells, the burden on a patient due to side effects of the adjuvant can be reduced. When the anti-cancer agent is locally administered, the anti-cancer agent can be allowed to act on tumor cells in a relatively short time and rather efficiently. Further, since the anti-cancer agent can be administered in a relatively small amount only at a necessary place, the relative burden on the patient can be reduced.

Note that, the present disclosure is not limited to the above-described embodiments, and various modifications can be made by those skilled in the art within the technical idea of the present invention. For example, in the treatment methods according to the first to sixth embodiments described above, the irradiation with the first near-infrared ray for the photolaser adjuvant is performed before the irradiation with the second near-infrared ray for photoimmunotherapy, but the irradiation with the second near-infrared ray may be performed before the irradiation with the first near-infrared ray. Alternatively, the operator may emit the second near-infrared ray while emitting the first near-infrared ray. The start and stop timings of the irradiation with the first near-infrared ray and the irradiation with the second near-infrared ray may be the same or different.

Further, the treatment methods according to the above-described embodiments may be appropriately combined. Therefore, the treatment method may include a combination of cancer immunotherapy, photoimmunotherapy, and administration of an anti-cancer agent.

The detailed description above describes embodiments of a treatment method for killing tumor cells. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A treatment method for killing a tumor cell, the method comprising:
    administering an antibody-photosensitive substance into a vein;
    inserting an endoscope from a mouth, a nose, or an anus and bringing the endoscope to a vicinity of a tumor having the tumor cell reachable from the mouth, the nose, or the anus after the administering of the antibody-photosensitive substance into the vein;
    placing an optical fiber into the tumor or in the vicinity of the tumor;
    irradiating at least one of the tumor, the vicinity of the tumor, or a regional lymph node with a first near-infrared ray by the optical fiber; and
    irradiating the antibody-photosensitive substance bound to a tumor cell membrane in the tumor cell with a second near-infrared ray after the irradiating of the at least one of the tumor, the vicinity of the tumor, or the regional lymph node with the first near-infrared ray, the second near-infrared ray having a shorter wavelength than that of the first near-infrared ray.

2. The treatment method according to claim 1, further comprising:
    inserting an elongated tube having a lumen into the endoscope;
    placing the elongated tube into contact with the tumor or puncturing the tumor with the elongated tube while checking a camera image and/or an ultrasound image obtained by the endoscope; and
    the placing of the optical fiber into the tumor or in the vicinity of the tumor is through the lumen of the elongated tube.

3. The treatment method according to claim 2, wherein a distal portion of the elongated tube has a light-transmitting portion capable of transmitting a near-infrared ray, the method further comprising:
    emitting one or more of the first near-infrared ray and the second near-infrared ray from the optical fiber located inside the elongated tube through the light-transmitting portion.

4. The treatment method according to claim 2, wherein a distal portion of the elongated tube has a slit through which a near-infrared ray can be emitted, the method further comprising:
    emitting one or more of the first near-infrared ray and the second near-infrared ray from the optical fiber located inside the elongated tube through the slit.

5. The treatment method according to claim 2, wherein the elongated tube has a needle tip, the method comprising:
    puncturing the tumor cell with the needle tip of the elongated tube.

6. The treatment method according to claim 2, wherein the elongated tube has a needle tip, the method comprising:
    placing the needle tip of the elongated tube in contact with the tumor cell.

7. The treatment method according to claim 1, further comprising:
    inserting the endoscope from the mouth, the nose, or the anus and bring the endoscope into the vicinity of the tumor having the tumor cell reachable from the mouth, the nose, or the anus, after 12 hours to 36 hours has elapsed from the administering of the antibody-photosensitive substance into the vein.

8. The treatment method according to claim 1, comprising:
    monitoring the tumor cell to which the antibody-photosensitive substance is bound while being irradiated with the second near-infrared ray with a temperature measurement device to detect a change in temperature of the tumor.

9. The treatment method according to claim 1, further comprising:
    monitoring the tumor cell to which the antibody-photosensitive substance is bound while being irradiated with the second near-infrared ray with a hardness measurement device to detect a change in hardness of the tumor.

10. The treatment method according to claim 1, wherein the treatment method is for treating pancreatic cancer, lung cancer, stomach cancer, duodenal cancer, esophageal cancer, and/or colon cancer.

11. The treatment method according to claim 1, further comprising:
selecting an irradiation direction of the first near-infrared ray from one or more of a direction orthogonal to an axial direction of the optical fiber, a direction towards a distal end of the optical fiber, and a direction between the direction orthogonal to the axial direction of the optical fiber and the direction towards a distal end of the optical fiber.

12. The treatment method according to claim 1, further comprising:
emitting the first near-infrared ray at a wavelength of about 1064 nm; and
emitting the second near-infrared ray at a wavelength of 660 nm to 740 nm with a dose of 1 $Jcm^{-2}$ to 50 $Jcm^{-2}$.

13. A treatment method for killing a tumor cell, the method comprising:
administering an antibody-photosensitive substance into a vein;
inserting an elongated tube in a lumen of an endoscope from a mouth, a nose, or an anus and bringing the elongated tube and the endoscope to a vicinity of a tumor having the tumor cell reachable from the mouth, the nose, or the anus after the administering of the antibody-photosensitive substance into the vein;
placing an optical fiber into the tumor or in the vicinity of the tumor via a lumen of the elongated tube;
irradiating at least one of the tumor, the vicinity of the tumor, or a regional lymph node with a first near-infrared ray by the optical fiber; and
irradiating the antibody-photosensitive substance bound to a tumor cell membrane in the tumor cell with a second near-infrared ray after the irradiating of the at least one of the tumor, the vicinity of the tumor, or the regional lymph node with the first near-infrared ray, the second near-infrared ray having a shorter wavelength than that of the first near-infrared ray.

14. The treatment method according to claim 13, further comprising:
acquiring a camera image and/or an ultrasound image with the endoscope during the placing of the optical fiber into the tumor or in the vicinity of the tumor.

15. The treatment method according to claim 13, wherein a distal portion of the elongated tube has a light-transmitting portion capable of transmitting a near-infrared ray, the method further comprising:
emitting one or more of the first near-infrared ray and the second near-infrared ray from the optical fiber located inside the elongated tube through the light-transmitting portion.

16. The treatment method according to claim 13, wherein a distal portion of the elongated tube has a slit through which a near-infrared ray can be emitted, the method further comprising:
emitting one or more of the first near-infrared ray and the second near-infrared ray from the optical fiber located inside the elongated tube through the slit.

17. The treatment method according to claim 13, wherein the elongated tube has a needle tip, the method comprising:
puncturing the tumor cell with the needle tip of the elongated tube or placing the needle tip of the elongated tube in contact with the tumor cell.

18. The treatment method according to claim 13, further comprising:
inserting the endoscope from the mouth, the nose, or the anus and bring the endoscope into the vicinity of the tumor having the tumor cell reachable from the mouth, the nose, or the anus, after 12 hours to 36 hours has elapsed from the administering of the antibody-photosensitive substance into the vein.

19. The treatment method according to claim 13, further comprising one or more of the following:
monitoring the tumor cell to which the antibody-photosensitive substance is bound while being irradiated with the second near-infrared ray with a temperature measurement device to detect a change in temperature of the tumor; and
monitoring the tumor cell to which the antibody-photosensitive substance is bound while being irradiated with the second near-infrared ray with a hardness measurement device to detect a change in hardness of the tumor.

20. The treatment method according to claim 13, wherein the treatment method is for treating pancreatic cancer, lung cancer, stomach cancer, duodenal cancer, esophageal cancer, and/or colon cancer, the method further comprising:
emitting the first near-infrared ray at a wavelength of about 1064 nm; and
emitting the second near-infrared ray at a wavelength of 660 nm to 740 nm with a dose of 1 $Jcm^{-2}$ to 50 $Jcm^{-2}$.

* * * * *